United States Patent
Rix et al.

(10) Patent No.: US 7,932,428 B2
(45) Date of Patent: Apr. 26, 2011

(54) PROCESS FOR PREPARING 1-BUTENE FROM TECHNICAL MIXTURES OF C4 HYDROCARBONS

(75) Inventors: Armin Rix, Marl (DE); Udo Peters, Marl (DE); Jochen Praefke, Marl (DE); Dirk Röttger, Recklinghausen (DE); Franz Nierlich, Marl (DE)

(73) Assignee: Evonik Oxeno GmbH, Marl (DE)

( * ) Notice: Subject to any disclaimer, the term of this patent is extended or adjusted under 35 U.S.C. 154(b) by 1199 days.

(21) Appl. No.: 11/521,460

(22) Filed: Sep. 15, 2006

(65) Prior Publication Data

US 2007/0149839 A1    Jun. 28, 2007

(30) Foreign Application Priority Data

Dec. 28, 2005   (DE) .................. 10 2005 062 700

(51) Int. Cl.
*C07C 5/25* (2006.01)
(52) U.S. Cl. .................. 585/664; 585/802; 585/327
(58) Field of Classification Search .................. None
See application file for complete search history.

(56) References Cited

U.S. PATENT DOCUMENTS

| | | | |
|---|---|---|---|
| 4,797,133 A | 1/1989 | Pujado | |
| 5,536,886 A * | 7/1996 | Tamminen et al. | ............ 568/697 |
| 6,657,090 B2 | 12/2003 | Rix et al. | |
| 7,002,053 B2 | 2/2006 | Nierlich et al. | |
| 2006/0264681 A1 | 11/2006 | Obenaus et al. | |

FOREIGN PATENT DOCUMENTS

DE    103 02 457 B3    10/2004

OTHER PUBLICATIONS

U.S. Appl. No. 11/624,823, filed Jan. 19, 2007, Rix et al.
U.S. Appl. No. 11/614,275, filed Dec. 21, 2006, Praefke et al.
U.S. Appl. No. 11/610,801, filed Dec. 14, 2006, Fernandez et al.

* cited by examiner

*Primary Examiner* — Tam M Nguyen
(74) *Attorney, Agent, or Firm* — Oblon, Spivak, McClelland, Maier & Neustadt, L.L.P.

(57) ABSTRACT

The invention relates to a process for preparing 1-butene from technical mixtures which comprise at least 1-butene, isobutene, n-butane and 2-butenes by partial conversion of the isobutene present, distillative removal of a fraction comprising 1-butene and isobutene, and conversion of the isobutene present therein to tert-butyl ethers.

32 Claims, 4 Drawing Sheets

PROCESS FOR PREPARING 1-BUTENE FROM TECHNICAL MIXTURES OF C4 HYDROCARBONS

CROSS REFERENCE TO RELATED APPLICATION

This application claims priority to German Patent Application No. 102005062700.5, filed Dec. 28, 2005, which is incorporated herein by reference in its entirety.

FIELD OF THE INVENTION

The invention relates to a process for preparing 1-butene from technical mixtures of $C_4$ hydrocarbons which comprise at least 1-butene, isobutene, n-butane and 2-butenes.

DISCUSSION OF THE BACKGROUND

1-Butene, as well as other $C_4$ hydrocarbons (such as isobutene and 2-butenes), is obtained in large amounts from technical $C_4$ cuts, for example the $C_4$ cut from steamcrackers or FCC units. These $C_4$ cuts comprise butadiene, the monoolefins isobutene and 1-butene, the two 2-butenes, and also the saturated hydrocarbons isobutane and n-butane. Owing to the small boiling point differences of the ingredients and their low separation factors, a distillative workup is difficult and uneconomic. Linear butenes are therefore usually obtained from other products by a combination of chemical reactions and physical separating operations.

The first step in obtaining linear butenes, which is common to all workup variants, when butadiene is present, is removal of most of the butadiene. The butadiene is either removed by an extractive distillation or chemically converted to butanes by selective hydrogenation. What remains, after either the extractive distillation or chemical conversion of butadiene, is a hydrocarbon mixture (so-called raffinate I or hydrogenated crack-$C_4$). The raffinate I comprises the saturated hydrocarbons n-butane and isobutane, the olefins isobutene and 1-butene, and cis and trans 2-butenes. Polyunsaturated $C_4$ hydrocarbons are present typically, in the raffinate I, in a fraction below 1%.

Because the boiling points of 1-butene and isobutene are very close together, it is not possible to remove 1-butene from the raffinate I, in an economically viable manner, by a simple distillation. Isobutene is therefore very substantially removed from the raffinate I by a selective chemical reaction. After the removal of the isobutene, a hydrocarbon mixture (raffinate II) remains. The raffinate II comprises linear butenes and the saturated hydrocarbons isobutane and n-butane. The components of raffinate II can be further separated by distillation, for example into isobutane and 1-butene, and a mixture of the two 2-butenes and n-butane. In further distillation steps, 1-butene which contains only small amounts of isobutene can be obtained in high purity from the 1-butenic fraction. Highly pure 1-butene is desirable because 1-butene is used to a large degree as a comonomer in ethylene polymerization, where isobutene impurities are undesired. Typical specifications of 1-butene therefore restrict the content of isobutene in the 1-butene to below 2000 ppm.

For the selective chemical reaction of the isobutene, which substantially removes isobutene from the raffinate I, various processes are known. One way of removing isobutene is to react the isobutene with alcohols, for example methanol or ethanol, to give the corresponding tertiary butyl ethers. The advantage of this reaction is that the isobutene can be converted virtually fully with high selectivity in the presence of linear butenes (without noticeable conversion of n-butenes occurring). For this purpose, various process technology variants have been developed. The technique of reactive distillation has been found to be particularly useful for achieving high isobutene conversions.

The industrially most significant process is the reaction of isobutene with methanol to give methyl tert-butyl ether (MTBE) which finds a great degree of use mainly as a fuel additive.

A further means of chemical conversion of the isobutene is the reaction with water to give tert-butyl alcohol (TBA). Owing to the low solubility of water in $C_4$ hydrocarbons, this route is technically more complex than the ether syntheses.

Another possibility for removing isobutene is to oligomerize the isobutene and remove the oligomerizate. A disadvantage of oligermizing isobutene is that a large portion of the linear butenes present are also, and undesirably, converted to cooligomers or homooligomers during the isobutene oligomerization. A further disadvantage is the partial isomerization of 1-butene to the cis and trans 2-butenes.

A further means of to remove isobutene, in the presence of other $C_4$ hydrocarbons, is to react isobuten with formaldehyde. The products obtained are processed further, to give, for example, isoprene.

Many of the known conversions of isobutene, for example the conversion to tert-butyl alcohol (TBA) or the conversion to isobutene oligomers, do not afford full isobutene conversion or, in the alternative, afford only poor selectivities, at high conversions, in the presence of linear butenes. An example of a solution proposed is a combination of these processes with a simultaneous (EP 0 048 893, DE 29 44 457) or subsequent conversion of the remaining isobutene to tert-butyl ethers.

U.S. Pat. No. 4,797,133 describes, inter alia, a process wherein in a first reaction isobutene is removed from the starting hydrocarbon mixture, (for example by reaction to give tert-butyl alcohol (TBA)), and the remaining residue is then converted to an ether in an etherification reaction.

DE 103 02 457 describes a process for preparing butene oligomers and tert-butyl ethers from isobutenic $C_4$ streams, in which the isobutene can be removed from a substantially butadiene-free $C_4$ hydrocarbon stream with only small losses of linear butenes. In this process, a portion of the isobutene is oligomerized, using an acid catalyst, in a first reaction step and then the remaining isobutene is removed in a second reaction step by reacting the remaining isobutene with alcohol to give a tert-butyl ether. The etherification reaction takes place in a reactive distillation column.

DE 25 21 964 describes a two-stage process for preparing alkyl tert-butyl ethers. In the first stage, isobutene in the reaction mixture is reacted with an alcohol to form an ether, and the resulting ether is then removed from the reaction mixture. The residue remaining after removal of the ether is conducted into a second reaction stage for the conversion of the remaining isobutene.

All processes which comprise a partial conversion of the isobutene followed by conversion of the remaining isobutene fraction from within the entirety of the $C_4$ hydrocarbons suffer from two disadvantages. Firstly, the large amounts of material that have to be conducted into the second reaction step, and secondly, the relatively low concentrations of isobutene in the mixture. Both disadvantages generally force the apparatus equipment to be of undesirably large size and also, in most cases, result in increased energy consumption.

SUMMARY OF THE INVENTION

Accordingly, one object of the present invention is to provide an improved process for obtaining 1-butene from a technical mixture of $C_4$ hydrocarbons.

BRIEF DESCRIPTION OF THE DRAWINGS

A more complete appreciation of the invention and many of the attendant advantages thereof will be readily obtained as the same become better understood by the reference to the following detailed description when considered in connection with the accompanying drawings, wherein:

The process according to the invention will be illustrated below with reference to the figures FIG. 1 to FIG. 6 and FIG. 9, without any intention that the process be restricted to the embodiments depicted there by way of example. The figures

FIG. 1 shows an embodiment of the invention for obtaining 1-butene. In the process, a technical mixture of $C_4$ hydrocarbons is introduced into stage (a). In stage (a), some of the isobutene present in the technical mixture is reacted. The reaction can be effected, for example, with water, alcohol, formaldehyde or with itself. The product of stage (a) is transferred into the separating stage (b) in which unconverted $C_4$ hydrocarbons III are removed from the products II, preferably by thermal separating processes. The unconverted $C_4$ hydrocarbons III are transferred into a stage (c) which can be realized, for example, by a simple distillation column. In this column, stream III is separated into a fraction IV which comprises isobutene, isobutane and 1-butene, and an isobutene-free or virtually isobutene-free fraction V which comprises 2-butenes and n-butanes. The fraction IV is transferred into the second reaction stage (d) in which the isobutene is reacted with alcohol VI to give alkyl tert-butyl ethers (ATBE). In a subsequent separating stage (e), the ATBE VII is separated from unconverted hydrocarbons VIII. These hydrocarbons VIII are transferred into stage (f) in which the 1-butene is separated by distillation from the remaining hydrocarbons.

FIG. 2 is a schematic diagram of a possible embodiment of process steps a) and b), the reaction of the isobutene in stage (a) being the oligomerization of isobutene (embodiment 3). The technical mixture I is first conducted into a first oligomerization reactor R-a1. The product from the first reactor is conducted into a second oligomerization reactor R-a2 (method with equal or different temperature, etc. possible). The effluent from the second oligomerization reactor is transferred into a distillation column K-b1 which is equipped with a condenser W-b2 for the top product and a bottom evaporator W-b1. A portion of the top product is returned into the column as reflux. The top product removed is the stream III which comprises unconverted $C_4$ hydrocarbons, and the bottom product obtained is the product II from the conversion of isobutene, which consists mainly of di- and trimers of isobutene.

FIG. 3 is a schematic diagram of a possible embodiment of process steps a) and b), the conversion of isobutene in stage a) being the synthesis of tert-butyl alcohol (TBA) (embodiment 1). The technical mixture I is fed into the first reactor R-a1 of a battery of three reactors into which water is also conducted. The reactor R-a1 has a recycle line, with which a portion of the reactor effluent can be returned into the feed stream to the reactor. The other portion of the reactor effluent from the first reactor is conducted into the second reactor R-a2, into which water is likewise conducted. The reactor effluent from the second reactor is conducted into the third reactor R-a3, into which water is likewise fed. The effluent from the third reactor is transferred into a distillation column K-b1 which is equipped with a condenser W-b2 for the top product and a bottom evaporator W-b1. A portion of the top product is returned as reflux into the column. The top product removed is the stream III which comprises unconverted $C_4$ hydrocarbons, and the bottom product obtained is the product II, mainly tert-butanol from the reaction of the isobutene with water, and excess water.

FIG. 4 is a schematic diagram of a possible embodiment of process steps a) and b), the conversion of the isobutene in stage (a) being the synthesis of alkyl tert-butyl ether (ATBE) (embodiment 2). The technical mixture I is fed into the first reactor R-a1 of a battery of two reactors, into which alcohol is also fed. The reactor R-a1 has a recycle line, with which a portion of the reactor effluent can be returned into the feed stream to the reactor. The other portion of the reactor effluent from the first reactor is conducted into the second reactor R-a2. The effluent from the second reactor is transferred into a distillation column K-b1 which is equipped with a condenser W-b2 for the top product and a bottom evaporator W-b1. A portion of the top product is returned as reflux into the column. The bottom product obtained is the product II, mainly tert-butyl ether from the reaction of the isobutene with alcohol, with or without residual amounts of alcohol. The top product removed is the stream D-b1 which comprises unconverted hydrocarbons, with or without alcohol. When the stream comprises alcohol, which is the case, for example, when methanol and ethanol are used, this stream is conducted into the bottom of an extraction column K-b2, into which an extractant, for example water, is fed in countercurrent through the inlet E-b1 disposed at the top and is withdrawn via the outlet E-b2 at the bottom of the column. At the top of the column, the product obtained from the extraction is the stream of hydrocarbons III unconverted in stage (a).

FIG. 5 shows one possible embodiment of stages c), d) and e). The hydrocarbon stream III from stage b) is fed into a distillation column K-c1 which is equipped with a bottom evaporator W-c1 and, at the top, with a condenser W-c2 and a decanter, and separated into a (virtually) isobutene-free fraction V comprising 2-butenes and n-butanes, which is removed at the bottom of the column, and a virtually n-butane and 2-butenes-free fraction IV which comprises isobutene and 1-butene and is, if appropriate, separated in a decanter from an aqueous phase D-c1. The top of the column is equipped in such a way that a portion can be returned as reflux into the column. The fraction IV is transferred into the reactor R-d1, into which alcohol is also fed, and isobutene present in fraction IV is converted to ATBE (stage d)). The effluent from the reactor R-d1 is fed into a column K-e1 which can be designed as the simple distillation column or, as shown here, as a reactive column. The effluent from the reactor is fed into the reactive distillation column K-e1 preferably below the reactive packing. The column K-e1 is equipped with a bottom evaporator W-e1 and a condenser W-e2 for the top product. The bottom product obtained from the column K-e1 is ATBE.

The top product D-e1 can be returned partly as reflux into the column. The other portion is transferred into the extraction column K-e2, into which an extractant, for example water, is fed via the inlet E-e1 disposed at the top and is withdrawn via the outlet E-e2 at the bottom of the column. At the top of the column, the product obtained from the extraction is the stream of hydrocarbons VIII unconverted in stage d) and, if appropriate, e).

FIG. 6

Figure 6:
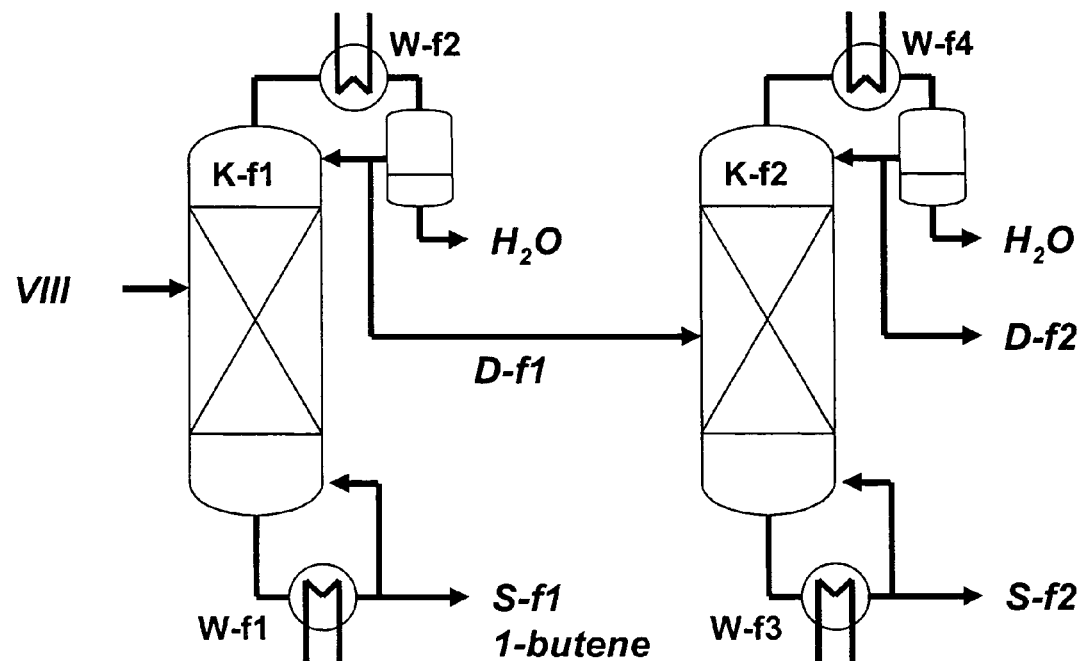

FIG. 6 is a schematic diagram of a possible embodiment of process step f). The hydrocarbon stream VIII from stage e) is fed into a distillation column K-f1. The column K-f1 is equipped with a bottom evaporator W-f1 and a condenser W-f2 for the top product. The bottom product obtained from the column K-f1 is 1-butene S-f1. The top product D-f1, from which water is removed in a decanter if appropriate, can be returned partly as reflux into the column. The other portion of the top product D-f1 is transferred into the distillation column K-f2. This column K-f2 too is equipped with a bottom evaporator W-f3 and a condenser W-f4 for the top product. The bottom product obtained from the column K-f2 is isobutane S-f2. The top product D-f2, from which water is removed in a decanter if appropriate, can be returned partly as reflux into the column. The other portion of the top product D-f2, which consists predominantly of low boilers, can be sent to a further use or to a thermal utilization.

The isobutane obtained in this workup (stream S-f2) may still comprise fractions of unsaturated components, mainly 1-butene. These can be hydrogenated in a downstream hydrogenation to the corresponding alkanes. This hydrogenation is effected by known industrial processes, preferably in the liquid phase over a palladium catalyst. Optionally, this hydrogenation can also be effected upstream of column K-f2; in this case, the stream D-f1 is fed first to the hydrogenation (not shown in FIG. 6) and then to the column K-f2.

FIG. 7

Figure 4:
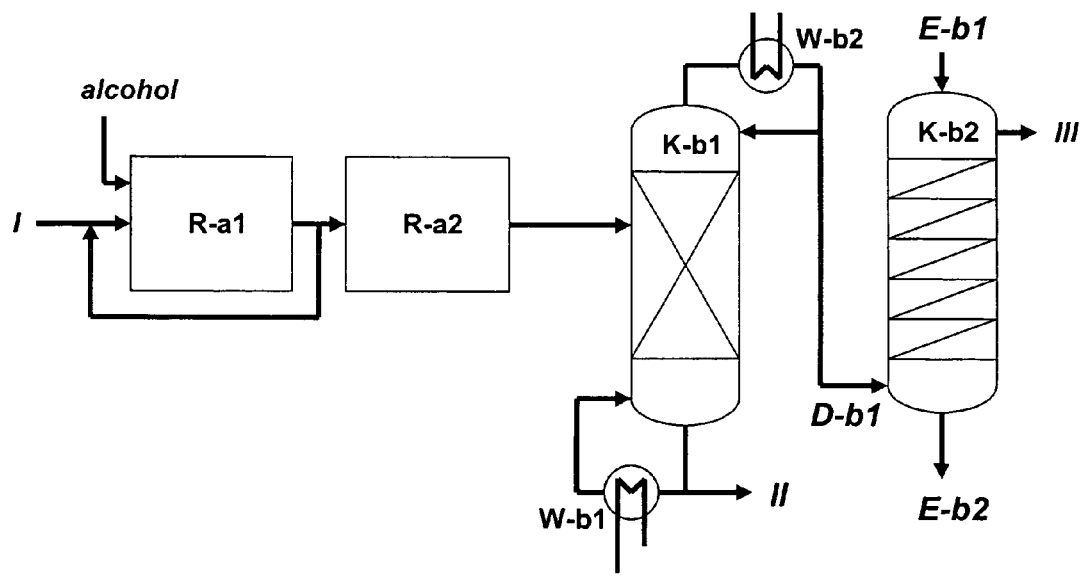
FIG. 4
Figure 7:
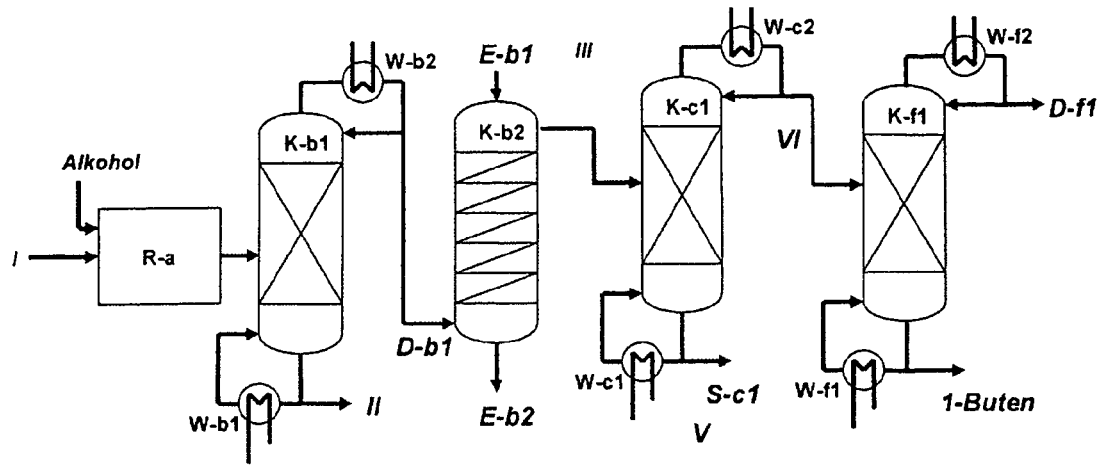
FIG. 7 and FIG. 8 show comparative variants. The schematic diagrams show only the essential stages. The illustration of streams customary for process technology purposes, for example cooling water streams, circulation streams, catalyst recyclings or return streams, and/or customary apparatus, for example heat exchangers or separators, has been dispensed with partly in favor of better clarity.

FIG. 7 shows the variant A of a one-stage process calculated in the comparative example. In this variant, stages (a) and (b) are carried out in an arrangement as shown in FIG. 4, a reactor system R-a being present in place of reactors R-a1 and R-a2. The product III obtained from the extraction column K-b2 is transferred into the distillation column K-c1 in which isobutane, isobutene and 1-butene are removed via the top. The bottom product S-c1 is obtained in a (virtually) isobutene-free fraction V comprising 2-butenes and n-butanes. The distillate VI of the column K-c1 is transferred directly into a further column K-f1 in which it is separated into a bottom product containing 1-butene and a top product comprising isobutane and/or low boilers. The bottom product obtained is a 1-butene-rich fraction which, however, contains the majority of the isobutene unconverted in R-a.

FIG. 8

Figure 1:
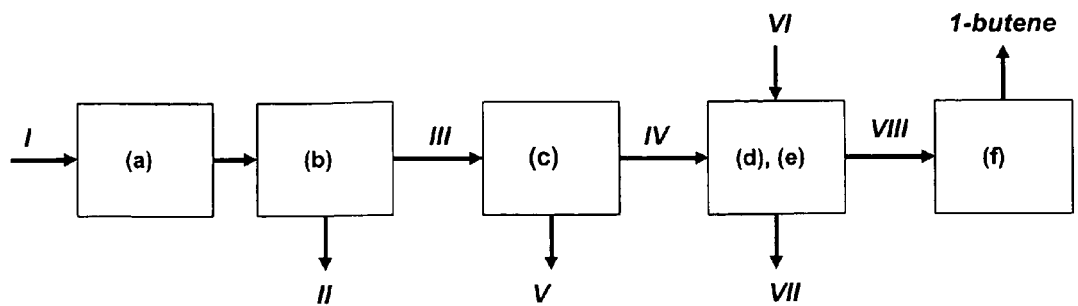
FIG. 1
Figure 2:
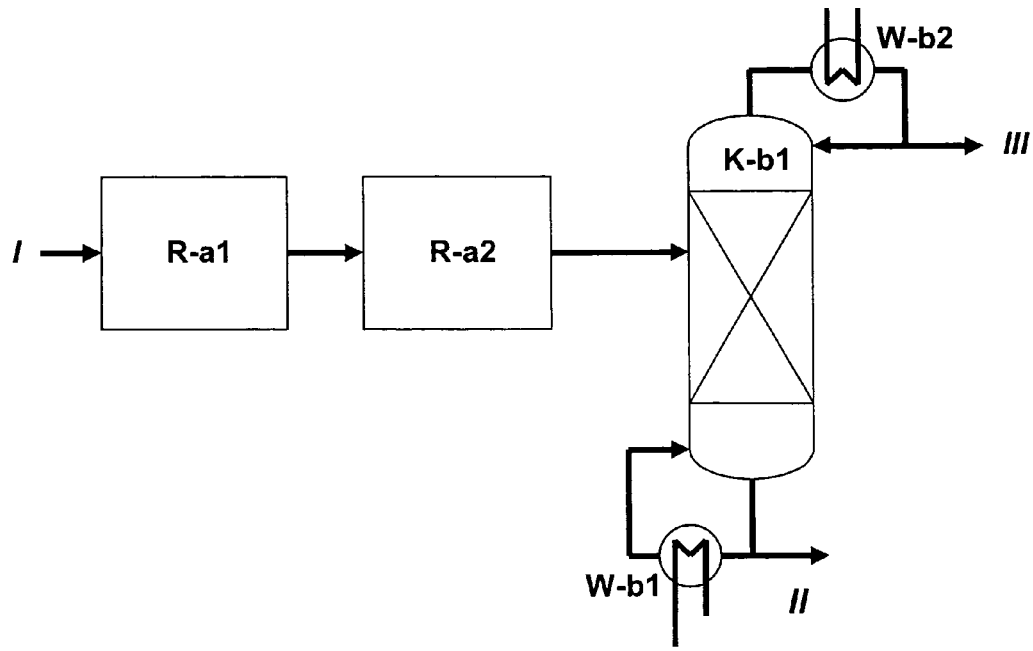
FIG. 2
Figure 3:
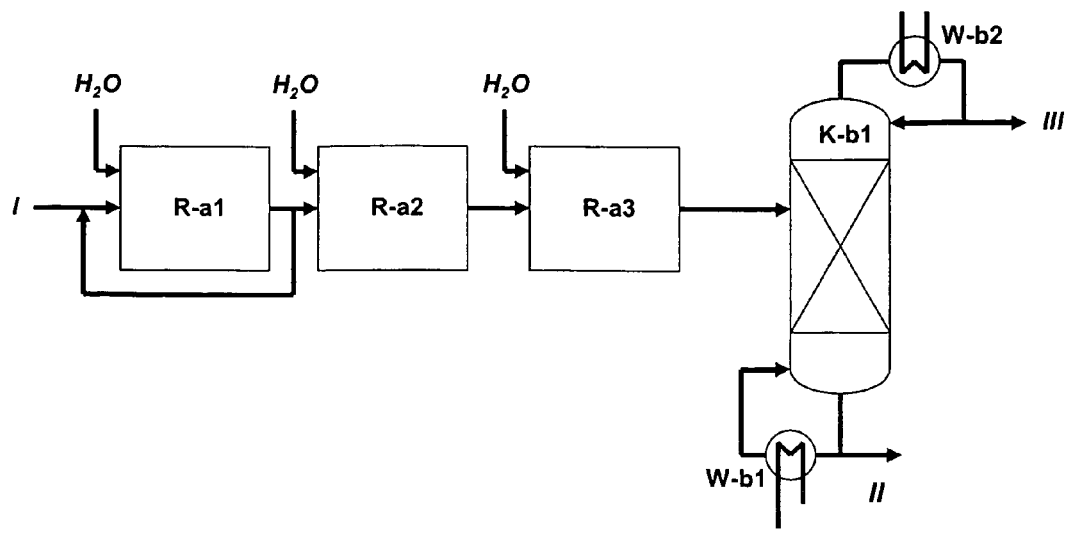
FIG. 3
Figure 8:
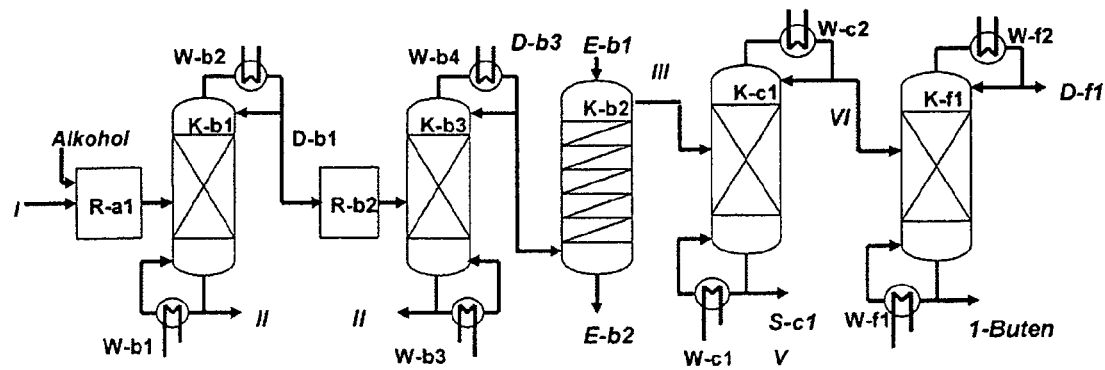

FIG. 8 shows the variant B of a two-stage process calculated in the comparative example. In this variant, stages (a) and (b) are carried out in an arrangement as shown in FIG. 3, a reactor R-a1 being present in place of reactors R-a1, R-a2 and R-a3. The distillatie D-b1 obtained from the column K-b1 is conducted directly into a second reactor R-b2 in which the remaining isobutene present in the distillate D-b1 is reacted with the alcohol which is likewise present. The reaction product from the reactor R-b2 is conducted into a column K-b3 in which the ether formed in R-b2 is removed from the remaining $C_4$ hydrocarbon stream D-b3 as the bottom product VII. The further workup of the distillate D-b3 is effected as shown in FIG. 7 for the distillate D-b1.

FIG. 9

Figure 5:
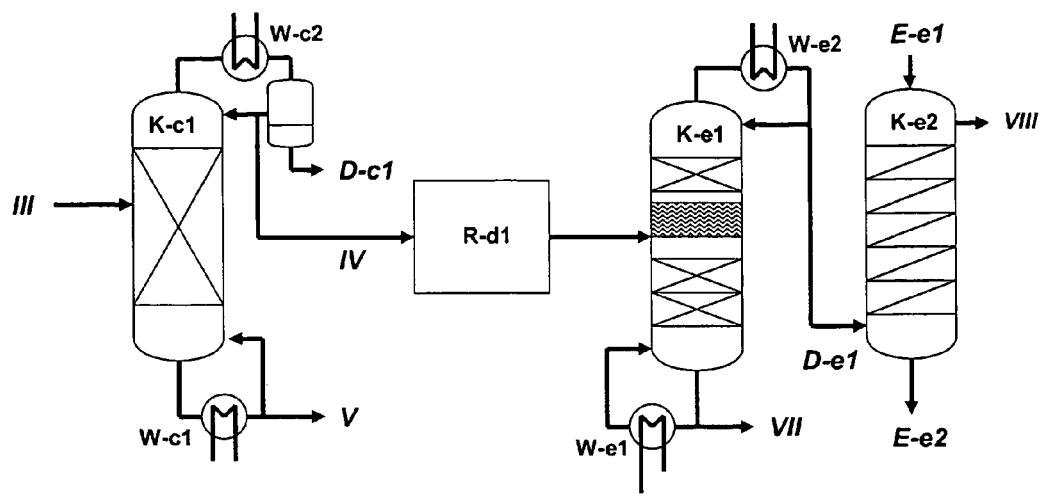
FIG. 5
Figure 9:
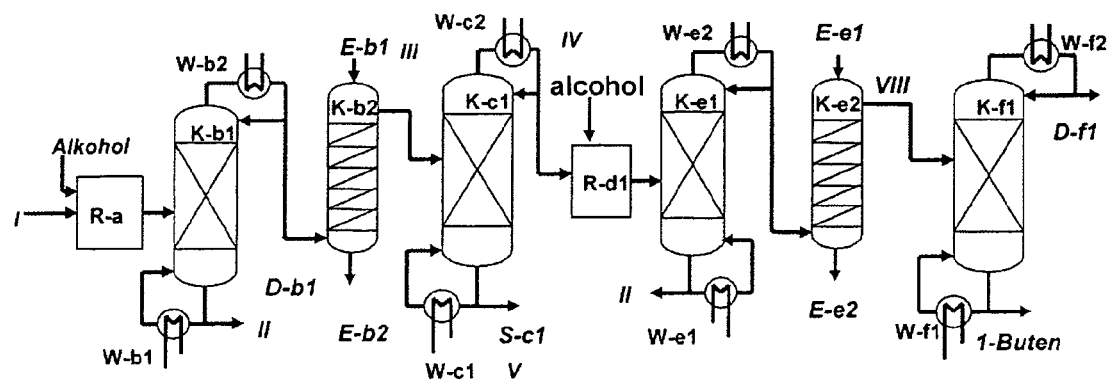

FIG. 9 is included to allow for comparison of an embodiment of the invention, as was used in the example, with the process variants according to FIGS. 7 and 8. FIG. 9 is a schematic diagram of an arrangement in which an etherification step is carried out both in stage (a) and in stage (d). Stages (a) and (b) are carried out in an arrangement as shown in FIG. 4, a reactor system R-a being present in place of reactors R-a1 and R-a2. The stages (c), (d) and (e) are carried out as described in FIG. 5. The product VIII which is obtained from the extraction column K-e2 is conducted into the distillation column, K-f1 in which it is separated into a bottom product containing 1-butene and a top product comprising isobutane and/or low boilers.

DETAILED DESCRIPTION OF THE PREFERRED EMBODIMENTS

It has now been found that, surprisingly, 1-butene can be obtained from a technical mixture of $C_4$ hydrocarbons, which contain at least 1-butene, isobutene, n-butane and cis and trans 2-butene, with only small losses of linear butanes. The 1-butene is obtained by the following process:

In a first reaction step a), a portion of the isobutene in the technical mixture of $C_4$ hydrocarbons is converted to products having a boiling point higher than 30° C.;

In a second step b), the remaining unconverted $C_4$ hydrocarbons are removed from the effluent of step a);

In a third step c), the unconverted $C_4$ hydrocarbons from b) are separated, by distillation, into a fraction comprising at least 1-butene and isobutene, and a virtually isobutene-free fraction comprising at least cis and trans 2-butenes and n-butane;

In a forth step d), reacting the isobutene present in the isobutene-containing fraction with an alcohol in the presence of an acidic catalyst to give an alkyl tert-butyl ether(s);

In a fifth step e), removing the unconverted $C_4$ hydrocarbons from the effluent of step d); and In a sixth step f), removing the 1-butene, by distillation, from the unconverted C4 hydrocarbons isolated in e).

The present invention therefore provides a process for preparing 1-butene from a technical mixture of $C_4$ hydrocarbons I which comprises at least 1-butene, isobutene, n-butane and 2-butenes, which is characterized by the process steps of:

a) Reacting a portion of the isobutene present in the technical mixture to give products II which boil at higher than 30° C. at standard pressure, b) Removing the unconverted $C_4$ hydrocarbons III from the effluent of stage a) by a thermal separation process, c) Distillatively separating the $C_4$ hydrocarbons III into a fraction IV comprising at least 1-butene and isobutene, and a virtually isobutene-free fraction V comprising at least 2-butenes and n-butane, d) Reacting the isobutene present in fraction IV with an alcohol VI in the presence of acidic catalysts to give tert-butyl ethers VII, e) Removing the unconverted $C_4$ hydrocarbons VIII from the effluent of stage d) and f) Distillatively removing the 1-butene from the $C_4$ hydrocarbons VIII obtained in e).

A particular advantage of the process according to the invention is that, by virtue of the additional removal of the 2-butenes and n-butanes from the reaction mixture in step c), a smaller volume stream has to be conducted through reaction step d), which is why the reactor(s) in process step d) can have a relatively small design or, with the same size, higher conversions can be achieved in comparison to conventional processes.

A further advantage of the removal of the 2-butenes and n-butanes in step c) is that the starting concentration of isobutene in step d) is correspondingly higher, which simplifies the reaction of the isobutene with alcohol in process step d).

In comparison to classical procedures, the reduced volume stream in stages d) to f) additionally gives rise to a significantly lower energy consumption of the overall process, for example, in the form of the heat carrier steam.

The process according to the invention can also be advantageously used when switching existing plants for preparing MTBE and 1-butene to preparing ethyl tert-butyl ether (ETBE) and 1-butene. Owing to the less favorable equilibrium position in the formation of ETBE from isobutene and ethanol, in comparison to the formation of MTBE from isobutene and methanol, there is a reduction in the isobutene conversion in the case of a simple alcohol change. The capacity losses which result from switching to preparing ETBE and 1-butene can advantageously be compensated for by switching to the process according to the invention.

The process according to the invention for preparing 1-butene from a technical mixture of $C_4$ hydrocarbons I which comprises at least 1-butene, isobutene, n-butane and 2-butenes has the process steps of
a) reacting a portion of the isobutene present in the technical mixture to give products II which boil at higher than 30° C. at standard pressure,
b) removing the unconverted $C_4$ hydrocarbons III from the effluent of stage a) by a thermal separation process,
c) distillatively separating the $C_4$ hydrocarbons III into a fraction IV comprising at least 1-butene and isobutene, and a virtually isobutene-free fraction V comprising at least 2-butenes and n-butane,
d) reacting the isobutene present in fraction IV with an alcohol VI in the presence of acidic catalysts to give tert-butyl ethers VII,
e) removing the unconverted $C_4$ hydrocarbons VIII from the effluent of stage d) and
f) distillatively removing the 1-butene from the $C_4$ hydrocarbons VIII obtained in e).

Process Step a)

The products II obtained in step a) by conversion of isobutene can be prepared, for example, by reacting isobutene with water, alcohols or formaldehyde, or by oligomerizing isobutene. To simplify removal of the products II from the remaining unconverted hydrocarbons, for example by distillation, the products II must have a boiling point at standard pressure (101 325 Pa) of greater than 30° C. The products II can be, for example, tert-butyl methyl ether (MTBE), tert-butyl ethyl ether (ETBE), tert-butanol (TBA), 3-methyl-3-buten-1-ol (MBOL), 4,4-dimethyl-1,3-dioxane or diisobutene. The products preferably have a boiling point at standard pressure of greater than 45° C. and preferentially greater than 50° C. The reactions in step a) are preferably carried out in such a way that the conversion of the isobutene in process step a) is of greater than 30%, preferably greater than 50%, preferentially of greater than 70% and more preferably greater than 80%. In the reaction of isobutene with water or an alcohol, the conversion is preferably greater than 75%. The magnitude of the conversion of isobutene can be controlled, for example, by the number of reactors used in step a) or by selection of suitable reaction conditions, which can be determined easily by the person skilled in the art by simple preliminary experiments.

Process Step b)

The unconverted $C_4$ hydrocarbons III are removed in step b) from the effluent of step a) by thermal separation processes, which should be understood in the context of the present invention to mean distillations and fractionations and extractions. When process step a) includes a reactive distillation, process step b) may take place at least partly actually in the course of performance of the reactive distillation, and a separate step b) can be dispensed with, if appropriate.

Process Step c)

After the removal in step b) of the products and of any unconverted compounds present which have been added as reactants in step a), the resulting hydrocarbon stream is separated by distillation in step c). The distillative separation is carried out in such a way that a fraction IV containing at least 1-butene and isobutene, and a virtually isobutene-free fraction V containing at least 2-butenes and n-butane and having preferably less than 5% by mass, preferentially less than 1% by mass and more preferably less than 0.1% by mass of isobutene are obtained. The fraction V contains at least 95% by mass, preferably at least 99% by mass, more preferably at least 99.8% by mass of the 2-butenes present originally in the hydrocarbon stream obtained as the product of step c). The fraction IV has preferably less than 1% by mass, more preferably less than 0.2% by mass of n-butane. The distillative separation can be carried out in apparatus used customarily for the separation of such hydrocarbon mixtures. Such apparatus may, for example, be distillation or fractionation columns.

Preference is given to carrying out the separation in a superfractionation column. The feed to this column is preferably in the lower half, preferably in the lower third of the column. Owing to the narrow boiling point of the mixture to be separated, the column is designed with preferably more than 100, preferentially more than 125, more preferably with 150 or more theoretical plates, and most preferably with from 150 to 200 theoretical plates. The reflux ratio (reflux rate to distillate withdrawal) is, depending on the number of stages realized and on the operating pressure, preferably less than or equal to 20, preferably less than 14, more preferably less than 11. The condensation can be carried out against cooling water or air. The distillate vessel is preferably designed as a liquid-liquid separator. This allows any water present in the feed stream to be removed as a second phase in the distillate vessel, and a technically water-free bottom product can be obtained.

The separation in process step c) is carried out preferably at a pressure of from 4 to 10 $bar_{absolute}$ (bara), preferably at a pressure of from 5 to 7 bara. The temperature at which the separation is carried out is preferably from 35 to 65° C., preferably from 40 to 50° C.

To heat the evaporator of the column, it is possible to use a typical heat carrier, for example steam or hot water. It is also possible to heat the evaporator of the column with waste heat from other processes. In the latter case, it may be advantageous to equip the column with more than one evaporator. The column is preferably equipped as a simple column with at least one evaporator and at least one condenser. Owing to the high energy demand and the small temperature difference between bottom and top of the column, energy-saving arrangements are particularly preferred embodiments. Reference is made here by way of example to the method of vapor compression. A further particularly preferred arrangement is two-pressure connection (double effect distillation) in integration with a second column. The second column may preferably be a parallel-connected column with the same or different separation tasks. One of the columns is operated at a sufficiently high pressure such that its condensation temperature is sufficient to heat the other column. In the arrangement of columns with different separating tasks for heating purposes, it is possible in principle for any suitable column from the process according to the invention, but also a column which is present outside the process according to the invention at the plant location, to be connected with the inventive column of process step c). The second column is more preferably the $C_4$ separating column from process step f).

The fraction V obtained in step c) can be used as an alkylating agent. In particular, it is suitable for preparing n-butene oligomers, in particular di-n-butene or tributene, for example by the OCTOL process of OXENO Olefinchemie GmbH, as described in DE 196 29 906 or EP 0 395 857.

Process Step d)

The isobutenic fraction IV obtained from step c) is converted in the process according to the invention in a further reaction step (step d) in which the remaining isobutene is converted by adding-on alcohol to give the corresponding tertiary ether.

The etherification of the isobutene is carried out as an acid-catalyzed reaction. The alcohol(s) used may be primary, secondary, mono- or polyhydric alcohol(s). The alcohol(s) preferably have from 1 to 5 carbon atoms. More preferably, the alcohol(s) are methanol or ethanol. The alcohol(s) used may be highly pure alcohol(s), pure alcohol(s) or alcohol(s) which have small amounts of impurities. The purity of the alcohol(s) used, reported in % by mass of alcohol, is over 90%, more preferably over 95%, most preferably over 99%. The content of water is preferably below 3% by mass, more preferably below 1% by mass, most preferably below 0.3% by mass.

For the reaction of isobutene with alcohol(s), in particular with methanol to give methyl tert-butyl ether, various process variants have been developed (cf.: Ullmann's Encyclopedia of Industrial Chemistry, Online Version, 2004, Wiley & Sons, under methyl tert-butyl ether, and literature cited there; Obenaus, Fritz; Droste, Wilhelm, Erdoel & Kohle, Erdgas, Petrochemie (1980), 33(6), 271-275; DE 26 29 769; DE 28 53 769). In principle, all known processes for reacting isobutene with alcohol(s) are suitable for use as process step d) in the context of the present invention.

Preference is given to using processes in which the reaction is effected in the liquid phase over an acidic ion exchange resin. The reactors in which the alcohol is reacted with the isobutene up to close to the thermodynamic equilibrium may be conventional fixed bed reactors (tube bundle reactors, adiabatic fixed bed reactors, circulation reactors). They may be operated with or without partial recycling, and any recycle stream may optionally be cooled.

The reactors may be operated at temperatures of from 10 to 160° C., preferably at temperatures of from 30 to 110° C. The pressure is preferably from 5 to 50 bara, preferably from 10 to 20 bara. Since the thermodynamic equilibrium between alcohol/isobutene and ether at low temperature is predominantly on the side of the ether, it is possible when using a plurality of reactors to operate the first of the reactors at higher temperature (high reaction rate) than the downstream reactors (exploitation of the equilibrium position).

The molar ratio of alcohol to isobutene in the feed to process step d) is preferably in the range from 10:1 to 1:1, more preferably from 5:1 to 1.1:1 and most preferably in the range from 3:1 to 1.2:1. The catalyst used, both in the fixed bed stages and in any reactive distillation column present, is a solid substance which is soluble neither in the feedstock mixture nor in the product mixture and has acidic sites on its surface. Under reaction conditions, the catalyst should not release any acidic substances to the product mixture, because this can lead to yield losses.

The activity of the catalyst is preferably selected such it catalyzes the addition of alcohol to isobutene under the reaction conditions, but barely catalyzes the addition of alcohol to linear butenes. Moreover, the catalysts should barely, if at all, catalyze the oligomerization of linear butenes and dialkyl ether formation from two molecules of alcohol. In order to achieve a high yield of 1-butene, the activity for the isomerization of 1-butene to 2-butene should preferably be low.

The solid catalyst may, for example, be zeolites, acid-activated bentonites and/or aluminas, sulfonated zirconium oxides, montmorillonites or acidic ion exchange resins.

A group of acidic catalysts preferred in the process according to the invention is that of solid ion exchange resins, especially those having sulfonic acid groups. Suitable ion exchange resins are, for example, those which are prepared by sulfonating phenol/aldehyde condensates or cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers which are formed by reaction of styrene with divinylbenzene are used as a precursor for the preparation of ion exchange resins with sulfonic acid groups. The resins may be in gel, macroporous or sponge form.

The properties of these resins, especially specific surface area, porosity, stability, swelling or shrinkage and exchange capacity, can be varied by virtue of the preparation process.

In the process according to the invention, the ion exchange resins can be used in their H form. Strongly acidic resins of the styrene-divinylbenzene type are sold, inter alia, under the following trade names: Duolite C20, Duolite C26, Amberlyst 15, Amberlyst 35, Amberlite IR-120, Amberlite 200, Dowex 50, Lewatit SPC 118, Lewatit SPC 108, K2611, K2621, OC 1501.

The pore volume is preferably from 0.3 to 0.9 ml/g, in particular from 0.5 to 0.9 ml/g. The particle size of the resin is preferably from 0.3 mm to 1.5 mm, in particular from 0.5 mm to 1.0 mm. The particle size distribution can be selected relatively narrowly or relatively widely. For example, ion exchange resins with very uniform particle size (monodisperse resins) can be used. The capacity of the ion exchanger is, based on the supply form, preferably from 0.7 to 2.0 eq/l, in particular from 1.1 to 2.0 eq/l, or preferably from 0.5 to 5.5 mol/kg, in particular from 0.8 to 5.5 mol/kg (the capacity data in mol/kg are based on the ion exchange resin dried in each case to constant weight in a hot nitrogen stream at, for example, 105° C.).

In a preferred embodiment, the addition of the alcohol to the isobutene is carried out in the presence of an acidic catalyst such that at least one reaction stage is carried out as a reactive distillation. More preferably, the acid-catalyzed etherification in step d) is carried out in at least two reaction stages, in which case preferably at least one, and more preferably the last reaction stage, is carried out as a reactive distillation. In the fixed bed reactor(s), a reaction mixture which is close to the thermodynamic equilibrium with regard to its isobutene, alcohol and tert-butyl ether concentration is first prepared over an acidic catalyst from the isobutenic fraction IV and the alcohol VI. The conversion of the isobutene is preferably greater than 90%. In the next/last reaction stage, this mixture is fed into the reactive distillation column, where a further portion of the isobutene is converted to ether.

In the reaction part of the reactive distillation column, the same catalysts may be used as those described above for a simple embodiment of the process stage without the use of a reactive distillation.

In the reactive distillation column, the catalyst may either be integrated in the packing, for example KataMax® (as described in EP 0 428 265), KataPak® (as described in EP 0 396 650 or DE 298 07 007.3), or polymerized onto moldings (as described in U.S. Pat. No. 5,244,929).

The reaction of the isobutene with alcohol to give the corresponding tertiary butyl ether is effected in the reactive distillation preferably in the temperature range from 10 to 140° C., preferentially at from 40 to 90° C., more preferably at from 60 to 80° C. (region of the column in which the catalyst is disposed. The bottom temperature of the column may be significantly higher).

In particular, isobutene is removed by reaction with methanol to give MTBE or with ethanol to give ETBE. For reaction of methanol with isobutene, the procedure is described in DE 101 02 082. The $C_4$ hydrocarbon mixture comprising isobutene is fed into the prereactor(s) together with alcohol (methanol or ethanol). The alcohol is preferably used in excess. In the prereactors, a mixture in which isobutene, alcohol (methanol, ethanol) and corresponding alkyl tert-butyl ether (ATBE) are present in equilibrium or virtually in equilibrium is formed. This reaction mixture is passed into the reactive distillation column.

In the feed of the reactive distillation column, more alcohol (methanol, ethanol) may be present than is needed for the full conversion of the isobutene still remaining. However, the alcohol excess should be such that a sufficient amount of alcohol is present for the azeotrope which forms from alcohol (methanol, ethanol) and $C_4$ hydrocarbons.

Optionally, for example when the alcohol content in the column feed is below the maximum permissible value, additional alcohol may be added to the column feed. In addition, alcohol may be fed in to the column by means of a separate device at the top of the reactive distillation column or at other points, for example directly above or in a liquid distributor of the catalytic packings.

The reactive distillation column preferably has, above the catalyst packing, a region of purely distillative separation. The zone above the catalyst packing has preferably from 5 to 20, in particular from 10 to 15 separating stages. The separating zone below the catalyst comprises from 12 to 36, in particular from 20 to 30 separating stages. The height of the catalyst zone/reactive zone can be determined as a function of the desired isobutene conversion by simple preliminary experiments. The amount of catalyst is preferably selected at such a level that an isobutene conversion of from 75 to 99%, preferably from 85 to 98% and more preferably from 95 to 97%, based on the isobutene content in the feed to the reactive distillation, is achieved.

The feed to the reactive distillation column may be above or below, preferably below the catalyst zone. The feed to the reactive distillation column is preferably below the reactive packing, preferably from 3 to 13, more preferably from 4 to 10 theoretical plates below the reactive packing.

The reactive distillation column is operated at pressures, measured at the top of the column, of from 3 bara to 25 bara, preferably from 5 bara to 15 bara, in particular from 7 bara to 10 bara. The hydraulic loading in the catalytic packing of the column is preferably from 10% to 110%, preferably from 20% to 70% of its flood point loading. The term "hydraulic loading" of a distillation column is understood to mean the uniform flow demand on the column cross section by the ascending vapor stream and the refluxing liquid stream. The upper loading limit indicates the maximum loading by vapor and reflux liquid, above which the separating action declines owing to entrainment or accumulation of the reflux liquid by the ascending vapor stream. The lower loading limit indicates the minimum loading, below which the separating action declines or collapses owing to irregular flow or emptying of the column—for example of the trays. (Vauck/Müller, "Grundoperationen chemischer Verfahrenstechnik"[Basic operations in chemical process technology], p. 626, VEB Deutscher Verlag für Grundstoffindustrie.)

At the flood point, the shear stresses transferred from the gas to the liquid become so great that the entire amount of liquid is entrained with the gas in the form of drops, or alternatively there is phase inversion in the column (J. Mackowiak, "Fluiddynamik von Kolonnen mit modernen Füllkörpern und Packungen für Gas/Flüssigkeitssysteme"[Fluid dynamics of columns with modern random packings and structured packings for gas/liquid systems], Otto Salle Verlag 1991).

The reactive distillation column is preferably operated with reflux ratios of from 0.2 to 4, in particular with those Which are from 0.4 to 2, preferably from 0.5 to 1.

When alcohols other than methanol and ethanol are used for the etherification, the parameters of the reactive distillation change correspondingly.

When a reactive distillation is used as the last step in stage d), it is possible for step d) and also step e), specifically the removal of the ATBE from the unconverted hydrocarbons, to take place at least in part therein. It is then possible, if appropriate, to dispense with a further step e).

The generic term "reactive distillation" includes all process technology measures in which distillation and reaction are carried out simultaneously. In the reactors described, this is achieved by a particular design of the packings in a column. It is also possible in the process according to the invention to spatially separate these regions without losing the advantages of a reactive distillation. In one process variant, the reactive distillation column is designed as a distillation column with one or more external reactor(s) which contain(s) the catalyst and is/are operated in a bypass stream.

Process Step e)

When no reactive distillation column is used in process step d) for etherification and simultaneous separation, a separate step e) has to be provided in the process according to the invention, in which the product from process step d) is separated into the alkyl tert-butyl ether and the unconverted hydrocarbons. The separation can be effected, for example, by feeding the effluent from the reactor of process step d) into a distillation column. The column may be equipped with a bottom evaporator and a condenser for the top product. The bottom product obtained from the distillation column is ATBE and any excess alcohol. The top product may be returned partly into the column as reflux. The other portion can be fed to process step f).

The column has preferably more than 20, preferentially more than 25, more preferably more than 30 theoretical plates. Depending on the number of stages realized, the reflux ratio is preferably less than or equal to 2, more preferably less than 1. The condensation can be carried out against cooling water or air. To heat the evaporator of the column, it is possible, for example, to use steam. It may be advantageous to pass the feed stream to the column into the column in at least partly preevaporated form or to flash it directly into the column. For this purpose, heat is supplied to the feed stream in an external heat transferer, for example by utilizing waste heat. To achieve partial evaporation, a kettle evaporator is the preferred embodiment of the heat transferee. It may also be advantageous when an intermediate evaporator heated to a lower temperature level with process or waste heat is used in the lower section of the column.

Irrespective of whether the step has been carried out in a distillation or reactive distillation column, when the top product of process step e) still comprises residual amounts of alcohol in the $C_4$ hydrocarbons, it may be advantageous to remove the alcohol in at least one additional process step. Processes for removing alcohols, in particular methanol or ethanol, are known. The removal can be effected, for example, by means of adsorption on molecular sieves, membrane processes, azeotroping agent distillations or extractions. The removal can be effected particularly elegantly in an extraction step by extraction of the alcohol with water. This scrubbing is effected by the known standard industrial processes, for example in an extraction column or in a battery of mixers and separating vessels. Compared to the other processes, it has various advantages, for example low capital cost and low operating costs.

When methanol or ethanol is used as the alcohol, residual amounts of the alcohol in the $C_4$ hydrocarbons are preferably removed in an extraction column with water. The residual content of alcohol in the $C_4$ hydrocarbons is preferably lowered to below 0.2%, more preferably to below 500 ppm, most preferably to below 50 ppm. The extraction column has preferably from 25 to 2, more preferably from 15 to 5 theoretical plates, and is preferably operated at temperatures of from 10 to 90° C. and pressures of at least one bar above the vapor pressure of the $C_4$ hydrocarbons.

The alcohol-laden scrubbing water from the extraction is preferably worked up in a separate unit and returned at least in part into the extraction. The workup can be effected, for example, by distillation in which a virtually alcohol-free water fraction is obtained in the bottom and an alcohol-rich fraction as the top product.

The top product of the distillation column or reactive distillation column is preferably transferred to an extraction column into which an extractant, for example water, is fed in countercurrent via a feed disposed at the top. The extractant may be withdrawn via the outlet at the bottom of the column. At the top of the column, the product obtained from the extraction is the stream of hydrocarbons unconverted in stage d) and, where present, e), VIII, which is fed to step f).

The alkyl tert-butyl ether obtained as a bottom product in the reactive distillation or distillation of steps d) and/or e) may still contain residual amounts of alcohol and may be utilized for various purposes. In addition to the use as a component for gasoline fuels, it finds use, for example, as a solvent. Isobutene of high purity is obtainable by dissociation of the tert-butyl ether.

The MTBE obtained when methanol is used is, for example, in addition to the use as a component in gasoline fuel, utilized as a solvent. To obtain MTBE of high purity, which is preferably used as a solvent, the MTBE obtained in the process can be purified further by distillation. This reduces the content of impurities present in a small amount (for example methyl sec-butyl ether, $C_8$ HC, TBA, alcohols).

The dissociation of MTBE to obtain isobutene is described, for example, in DE 100 20 943. The purity of the isobutene obtained in this way is dependent upon on factors including the fraction of methyl sec-butyl ether in the MTBE. Depending on the requirements, MTBE prepurified to a different level of intensiveness is used for the dissociation.

In a preferred embodiment of the process, the reaction in step d) is conducted with a stoichiometric excess of alcohol and the bottom product which is obtained in the reactive distillation or distillation of steps d) and/or e) and which contains alkyl tert-butyl ether and residual amounts of alcohol is returned fully or partly into step a) and/or b). The ratio of alcohol to isobutene which is conducted into step d) is from 1.1 to 10 mol/mol, preferably from 1.2 to 5 mol/l. In this variant in step d), the reaction is preferably carried out only in fixed bed reactors and a distillative separation in a distillation column is carried out in step e). The unconverted $C_4$ hydrocarbons VIII are obtained as a top product and the bottom product obtained, which comprises at least tert-butyl ether and residual amounts of alcohol, is returned fully or partly into step a) and/or b).

Process Step f)

1-Butene is removed by distillation from the $C_4$ hydrocarbon mixture VIII that has been obtained from the reactive distillation or distillation in step e), that may have been freed of alcohol, and that consists of unconverted hydrocarbons which comprise essentially 1-butene, isobutane and low boilers. The 1-butene is removed by distillation of the mixture VIII in one or more distillation columns.

In a preferred embodiment, the 1-butene is removed in a distillation column in which very pure 1-butene is obtained as the bottom product. The top product obtained is an isobutane-rich fraction which additionally contains low boilers (for example $C_3$ hydrocarbons).

The separation is preferably carried out in a superfractionating column. The feed to this column is preferably into the upper half, more preferably into the lower half of the upper half of the column. Owing to the narrow boiling point of the mixture to be separated, the column is preferably designed with more than 100, preferentially more than 125, more preferably more than 150 and most preferably from 1.50 to 200 theoretical plates. The reflux ratio (reflux rate to distillate removal) is, depending on the number of stages realized and on the operating pressure, preferably less than or equal to 100, preferentially less than 70, more preferably less than 60. Most preferably, the reflux ratio is from 30 to 60. The condensation can be carried out against cooling water or air. The distillate vessel is preferably designed as a liquid-liquid separator. This allows any water present in the feed stream to be removed as a second phase in the distillate vessel, and a technically water-free bottom product can be obtained.

To heat the evaporator of the column, it is possible to use a typical heat carrier, for example steam or hot water, and also preferably waste heat from other processes. In the latter case, it may be advantageous to equip the column with more than one evaporator. The column is preferably equipped as a simple column with at least one evaporator and at least one condenser. Owing to the high energy demand and the small temperature difference between bottom and top of the column, energy-saving arrangements are particularly preferred embodiments. Reference is made here by way of example to the method of vapor compression. A further particularly preferred arrangement is two-pressure connection (double effect distillation) in integration with a second column. The second column may preferably be a parallel-connected column with the same or different separation tasks. One of the columns is operated at sufficiently high pressure that its condensation temperature is sufficient to heat the other column. In the arrangement of columns with different separating tasks for heating purposes, it is possible in principle for any suitable column from the process according to the invention, but also a column which is present outside the process according to the invention at the plant location, to be connected with the inventive column of process step f). The second column is more preferably the $C_4$ separating column from process step c). One of the columns is operated at sufficiently high pressure that its condensation temperature is sufficient to heat the other column.

In a further preferred embodiment of process step f), low boilers are removed as the top product in a first distillation column; in the bottom of the column, a mixture which comprises mainly 1-butene and isobutane is obtained. In a second column, this bottoms mixture is separated into 1-butene, which is obtained as the bottom product, and an isobutane-rich fraction (top product).

Pure 1-butene prepared by the process according to the invention contains preferably less than 5000 ppmw (ppm by mass), preferentially less than 2000 ppmw and more preferably less than 1500 ppmw of isobutene, and is a sought after intermediate. It is used, for example, as a comonomer in the preparation of polyethylene (LLDPE or HDPE) and the preparation of ethylene-propylene copolymers. Pure 1-butene also finds use as an alkylating agent and is a starting material for the preparation of butan-2-ol, butene oxide, valeraldehyde. A further use of the virtually isobutene-free 1-butene prepared in accordance with the invention is the preparation of n-butene oligomers, in particular by the Octol process.

In process step f), isobutane-rich fractions are typically obtained in addition to the 1-butene (depending on the starting composition of the $C_4$ hydrocarbons). These may be worked up further, preferably to give pure isobutane. The isobutane obtained in the workup preferably has a purity of at least 90% by mass of isobutane, more preferably 95% by mass of isobutane, and contains preferably less than 1000 ppmw, more preferably less than 200 ppmw of olefins. Purification to give pure isobutane can be effected, for example, by full hydrogenation of the alkenes still present to alkanes and subsequent distillation.

Embodiment 1

Reaction of Isobutene with Water in Step a)

In a first preferred embodiment of the process according to the invention, the isobutene present in the technical $C_4$ hydrocarbon mixture is reacted in step a) with water to give tert-butanol (TBA). Step a) can be carried out such that the process is employed for preparing TBA. Preferred processes for reacting isobutene with water to give TBA employ a heterogeneous catalyst. Such processes are described, for example, in DE 10 2004 030 943, DE 103 30 710, EP 0 579 153, U.S. Pat. No. 6,111,148 or DE 30 25 262.

The preparation of tertiary butanol (TBA) by reacting the isobutenic $C_4$ hydrocarbon stream I with water is effected preferably over an acidic ion exchange resin. Step a) may take place in one, two or more reactors. It may also be advantageous when at least one process stage, preferably the last process stage of the preparation of TBA in step a), comprises a reactive distillation.

Preference is given to employing a process for reacting isobutene with water in which the reaction is effected in a plurality of steps over an acidic ion exchange resin. Preferably only one liquid phase is present. The $C_4$ hydrocarbons, water and optionally a cosolvent which boils at a temperature higher than the boiling point of $C_4$ hydrocarbons, preferably TBA, are introduced into the first stage. The cosolvent allows the fraction of water in the mixture to be increased without two liquid phases forming.

Since the hydration of isobutene consumes water, the water content in the reaction mixture falls. In order to obtain a maximum yield and/reaction rate, it may therefore be advantageous, when a plurality of reaction stages are present, to meter in water in each case before the downstream stages.

According to the invention, preferably only homogeneous solutions are fed to the reactors. Therefore, water or water-tert-butanol solutions have to be mixed with the starting hydrocarbon mixture or a reactor effluent, so that a homogeneous solution has formed by the time it enters the first reactor or one of the downstream reactors. This can be achieved, for example, using static mixers. The desired water concentration in the reactor feed can be established by quantitative control of the individual streams after measurement of their water contents.

The amount of water metered into the individual stages is preferably such that a single liquid phase is present at the reactor inlet. Preference is given to using a water content of from 30 to 100% by mass, more preferably from 70 to 98% by mass, of the amount of water possible by virtue of the solubility of water in the reaction mixture.

The process according to the invention can be carried out in batchwise or continuous reactors which are typically used in solid/liquid contact reactions. In the case of use of continuous flow reactors, a fixed bed is usually but not exclusively used. When a fixed bed flow reactor is used, the liquid can flow upward or downward. Preference is usually given to downward flow of the liquid.

It is also possible to operate the reactor with product recycling or in straight pass.

When tubular reactors are employed, the ratio of length to diameter of the catalyst bed can be varied, either by means of the geometric dimensions of the reactor or by means of its fill level. In the case of equal amount of catalyst and loading (LHSV), it is thus possible to achieve different superficial velocities. Reactors in which a portion of the reaction mixture is recycled can be operated with superficial velocities of preferably from 10 to 30 m/h. In the reactors which are flowed through in straight pass, the superficial velocities may preferably be in the range from 1 to 20 m/h.

Accordingly, the catalyst loading (LHSV) in the case of reactors which are operated with product recycling is preferably from 0.3 to 20 $h^{-1}$, preferentially from 1 to 10 $h^{-1}$. In the case of reactors which are flowed through in straight pass, the loadings are preferably in the range from 0.1 to 5.0 $h^{-1}$, preferably in the range from 0.4 to 3 $h^{-1}$.

The process according to the invention may be carried out in one reactor, but also in a plurality of reactors (in particular 2, 3 or 4 reactors) connected in series which may have temperatures falling in flow direction.

When the first reactor or a plurality of reactors is/are operated with product recycling, preference is given to setting a circulation factor (the term "circulation factor" refers to the ratio of amount pumped in circulation to fresh feed) of from 0.1 to 10. The circulation factor for the first reactor is preferably from 1 to 4, in particular from 2 to 3.5.

A preferred process variant consists in operating the first reactor with product recycling and the further reactors in straight pass. The number of reactors used is, depending on the conversion desired, preferably from 2 to 10, in particular from 2 to 4.

Each reactor can be operated adiabatically or virtually isothermally, i.e. with a temperature rise below 10° C. Too high a temperature rise is to be avoided owing to the unfavorable influence on the equilibrium (dissociation) and possibly by-product formation.

The temperatures at which step a) of the process according to the invention is carried out are preferably from 30 to 120° C. The reaction rate is too low at lower temperatures and an increased level of side reactions, for example oligomerization of the olefins, occurs at higher temperatures. The reactors are preferably operated in the 35 to 70° C. temperature range. The temperatures in different reactors may be the same or different within the range specified. One process variant consists in lowering the temperature in flow direction from reactor to reactor. Since the equilibrium position becomes more favorable with falling temperature, it is thus possible to achieve a higher conversion. However, it is not viable to lower the temperature below 35° C., since the reaction then becomes too slow for an industrial process.

The inventive reaction according to this embodiment of process step a) is preferably carried out at a pressure equal to or above the vapor pressure of the starting hydrocarbon mixture at the particular reaction temperature, preferably at a pressure below 40 bar. In order to avoid evaporation problems in the reactors, the pressure should preferably be at least 2 to 4 bar higher than the vapor pressure of the reaction mixture.

The overall conversion of isobutene depends upon the type and amount of the catalyst used, the reaction conditions established and number of reaction stages. For economic reasons, the isobutene conversion is normally kept within the range from 50 to 95%, preferably between 70 and 90%.

In process step b) of the process according to the invention, the removal of the unconverted $C_4$ hydrocarbons III from the products II, is preferably effected by distillation, in particular by feeding the reaction mixture leaving the last reactor into a distillation column which works at or below the pressure of the last reactor, but at least at a pressure of above 1 bar. In the distillation, the top product obtained is the unconverted hydrocarbons III. Since the $C_4$ hydrocarbons form azeotropes with water, a polar, aqueous phase is additionally obtained in the condensation of the vapors at the top of the column as well as the $C_4$ hydrocarbons. This is preferably removed. The removal is done by standard industrial processes, for example in a top decanter. Preference is therefore given to removing the $C_4$ hydrocarbons III from the TBA/water mixture together with a little water. The hydrocarbons III can be used in process step c) of the process according to the invention before or after the water removal, preferably after the water removal.

The bottom product obtained is an aqueous tert-butanol solution. A portion of the bottom product is preferably returned (recycled) into process step a), preferably into the first reactor of process step a). Preference is given to recycling from 0.1 to 2 t, more preferably from 0.2 to 0.5 t of bottom product per tonne of $C_4$ hydrocarbons fed.

The bottom product may be used as such or worked up further. Typical further workups are effected to tert-butanol (anhydrous) and the azeotrope of water and tert-butanol. For the preparation of anhydrous tert-butanol, the literature discloses several processes (DE 102 41 762 and references cited there).

It is also possible to recycle another stream which consists of water and tert-butanol and is obtained in the workup of the crude tert-butanol into process step a), preferably into the first reactor of process step a).

When a cosolvent is used, it will also be obtained in the bottoms of the distillation owing to the boiling point. It can be removed from the bottom product by means of suitable thermal separating processes and recycled fully or partly into process step a), preferably into the first reactor of process step a).

The actual catalyst used in all (both) stages of this embodiment of process step a) is a solid substance which is soluble neither in the feedstock mixture nor in the product mixture and has acidic sites on its surface. Preference is given to using a catalyst as described in process step d) as the catalyst in this embodiment of process step a). The catalyst can be used in all usable reactors, i.e., for example, both in fixed bed reactors and in the reaction part of reactive distillation columns. Acidic catalysts usable in this process variant are preferably solid ion exchange resins with sulfonic acid groups. In the inventive embodiment of step a), the ion exchange resins may be used in their H form. Strongly acidic resins of the styrene-divinylbenzene type are sold, inter alia, under the following trade names: Lewatit SCP 118, Lewatit SCP 108, Amberlyst 15 or Amberlyst 35, Lewatit K2621, Lewatit K2629, Lewatit K2431. The pore volume is preferably from 0.3 to 0.9 ml/g, in particular from 0.5 to 0.9 ml/g. The particle size of the resin is preferably between 0.3 mm and 1.5 mm, in particular between 0.5 mm and 1.0 mm. The particle size distribution may be selected relatively narrowly or relatively widely. For example, ion exchange resins with very uniform particle size (monodisperse resins) may be used. The acid capacity of the ion exchanger is, based on the supply form, preferably from 0.7 to 2.0 eq/l, in particular from 1.1 to 2.0 eq/l or preferably from 0.5 to 5.5 mol/kg, in particular from 0.8 to 5.5 mol/kg (the capacity data in mol/kg are based on the ion exchange resin dried in each case to constant weight in a hot nitrogen stream at, for example, 105° C.).

In a further preferred variant of embodiment 1, the last stage is performed as a reactive distillation. A process for preparing TBA via the process of reactive distillation is described, for example, in DE 102 60 991.

The isobutenic $C_4$ hydrocarbon stream and the water or the mixture of $C_4$ hydrocarbon stream, TBA and water is fed into the reactive distillation column preferably below the reaction zone. A distillative region may be present between feed and reaction zone. Below the reactive region is disposed a purely distillative region which serves to remove the TBA and any excess water. The bottom product of the reactive distillation contains predominantly TBA and water, ideally with water concentrations lower than in the water/TBA azeotrope. Optionally, a further distillative region can follow above the reactive region in order to adjust the isobutene concentration in the reaction zone. The top product obtained is the unconverted $C_4$ hydrocarbons III. In this variant, process step b) is thus part of step a).

Since the $C_4$ hydrocarbons form azeotropes with water, a polar aqueous phase is additionally obtained in the condensation of the vapors at the top of the column as well as the $C_4$ hydrocarbons III. This is preferably removed, and optionally recycled fully or partly into the column. The removal is effected in accordance with the standard industrial processes, for example in a top decanter. This process variant has the advantage that the water of reaction is substantially circulated and the top product of the column contains only small amounts of water. Optionally, a portion of the organic distillate phase or a portion of the entire distillate can be recycled into the reactive distillation column. The aqueous distillate phase can be recycled above and/or below the reaction zone, and the organic distillate phase above the reaction zone. The $C_4$ hydrocarbons III obtained in this way are typically water-saturated but free of heterogeneous water fractions. They can thus be used in process step c) of the process according to the invention.

The feed to the reactive distillation contains preferably less than 20% by mass, in particular less than 15% by mass of isobutene which is converted selectively to TBA in the reactive distillation column.

When the isobutenic stream is fed with water into the reactive distillation column below the reactive packing, the low-boiling $C_4$ hydrocarbons rise in vaporous form into the reaction zone and, owing to the minimum azeotrope of water and $C_4$ hydrocarbons, a portion of the water is also transported in vaporous form with the reactant into the reaction zone. Any TBA present in the feedstock mixture and parts of the water remain in the bottoms and are removed.

In the rectifier column, the reactive distillation column contains the catalyst; above and below the catalyst packing may be disposed separating trays and/or distillation packings. The catalyst is either integrated in a packing, for example KataMax® (EP 0 428 265), KataPak® (EP 0 396 650 or DE 298 7 007.3), or polymerized onto moldings (U.S. Pat. No. 5,244,929). Preference is given to using catalytic packings having a high catalyst content, for example Katapak-SP 12 or more preferably Katapak-SP 11.

The generic term reactive distillation includes all process technology measures in which distillation and reaction can be carried out integrated in material and energetic terms. In the catalyst packings described, this is achieved by the immobilization of the packings in the column. It is also possible in the process according to the invention to spatially separate these regions without losing the advantages of a reactive distillation.

In one process variant, the reactive distillation column is designed as a distillation column with one or more external reactors which contain the catalyst and are operated in a bypass stream.

The reactive rectification column, in which isobutene is converted and in which a TBA-rich stream is drawn off as the bottom product, preferably has a number of separating stages of from 2 to 60, in particular from 3 to 50. Preferably from 5 to 58 separating stages are accounted for by the stripping section, from 2 to 55 separating stages by the reaction zone and from 0 to 20 separating stages by the rectifier section above the reaction zone. Additional water can be metered into the column at all points. Preference is given to introducing water and prereacted mixture at the same position.

The operating pressure of the reactive distillation column, measured at the top of the column, is between 3 and 30 bara, in particular between 4 and 12 bara. The reflux ratio is in the range from 0.5 to 40, in particular in the range from 0.9 to 20.

Embodiment 2

Reaction of Isobutene with Alcohol in Step a)

In a preferred embodiment 2) of the process according to the invention, the isobutene from the isobutenic technical hydrocarbon mixture is reacted in step a) under acidic catalysis with alcohol to give alkyl tert-butyl ether (ATBE, also referred to as tert-butyl alkyl ether). In this embodiment of the process according to the invention, the reaction of isobutene with alcohol may be over 90%, preferably over 95%. The alcohol used may in particular be methanol or ethanol.

The etherification of the isobutene is carried out as an acid-catalyzed reaction. The alcohol(s) used may be primary, secondary, mono- or polyhydric alcohol(s), preferably having from 1 to 5 carbon atoms, more preferably the alcohols are methanol or ethanol. The alcohol(s) used may be highly pure alcohol(s), pure alcohol(s) or alcohol(s) which have small amounts of impurities. The purity of the alcohol(s) used, reported in % by mass of alcohol(s), is preferably over 90%, more preferably over 95%, most preferably over 99%. The content of water is preferably below 3% by mass, more preferably below 1% by mass, most preferably below 0.3% by mass. If ethanol is used, the ethanol can be dewatered in a conventional manner by azeotropic distillation or by membrane processes.

For the reaction of isobutene with alcohols, in particular with methanol to give methyl tert-butyl ether, various process variants have been developed (cf.: Ullmann's Encyclopedia of Industrial Chemistry, Online Version, 2004, Wiley & Sons, under methyl tert-butyl ether, and literature cited there; Obenaus, Fritz; Droste, Wilhelm, Erdoel & Kohle, Erdgas, Petrochemie (1980), 33(6), 271-275; DE 2629769; DE 2853769). In principle, all processes for reacting the isobutene with alcohols are suitable as process step a) in the context of this invention. Preference is given to processes in which the reaction is effected in the liquid phase over an acidic ion exchange resin. The reaction of isobutene with alcohol can be effected as described in process step d). The reactors in which the alcohol is reacted with the isobutene up to close to the thermodynamic equilibrium may be conventional fixed bed reactors (tube bundle reactors, adiabatic fixed bed reactors, circulation reactors, etc). The reactors may be operated with or without partial recycling, and the recycle stream may be cooled, if appropriate.

In a preferred embodiment, the reaction of the isobutene is carried out in at least two stages, in which case the first stage is conducted as an adiabatic fixed bed reactor with recycling and the downstream stages are conducted as fixed bed stages without recycling and/or as a reactive distillation. The ratio of amount recycled to fresh feed ($C_4$ hydrocarbons and alcohol) is preferably from 0.5 to 20 t/t, more preferably from 1 to 5 t/t. The reactors may be operated at temperatures of preferably from 10 to 160° C., preferentially from 30 to 110° C. The pressure in the fixed bed stages is preferably from 5 to 50 bara, preferably from 10 to 20 bara. Since the thermodynamic equilibrium between alcohol/isobutene and ether at low temperature is predominantly to the side of the ether, it is preferred when using a plurality of reactors to operate the first of the reactors at higher temperature (high reaction rate) than the downstream reactors (exploitation of the equilibrium position).

In this embodiment of the inventive process step a), the molar ratio of alcohol to isobutene is preferably from 5:1 to 0.9:1, preferably from 2:1 to 1:1 and more preferably from 1.5:1 to 1:1. Since a low conversion of isobutene can be accepted in process step a), a lower alcohol excess may be advantageously employed compared to process step d).

In a preferred embodiment, the addition of the alcohol onto the isobutene in the presence of an acidic catalyst is effected such that at least one reaction stage is carried out as a reactive distillation. More preferably, the acid-catalyzed etherification in step a) is carried out in at least two reaction stages, in which case preferably at least one stage, more preferably the last reaction stage, is carried out as a reactive distillation. In the fixed bed reactor(s), a reaction mixture which is close to the thermodynamic equilibrium with regard to its isobutene, alcohol and tert-butyl ether concentration is first prepared over an acidic catalyst from the isobutenic technical hydrocarbon mixture I and alcohol. The conversion of the isobutene is preferably greater than 90%. This mixture is fed into the reactive distillation column in the next/last reaction stage, where a further portion of the isobutene is converted to the ether.

The catalyst used both in the fixed bed stages and in the reactive distillation column is a solid substance which is not soluble in the feedstock mixture and the product mixture. The catalyst has acidic sites on its surface. Under reaction conditions, the catalyst should not release any acidic substances to the product mixture because this can lead to yield losses. The catalysts used may preferably be those as described in process step d), in which case the process according to the invention can be performed in such a way that the same catalyst or different catalysts can be used in each case in step a) and d). Preference is given to using the same catalysts in step a) and d).

In the reactive distillation column, the catalysts may either be integrated in the packing, for example KataMax® (as described in EP 0 428 265), KataPak® (as described in EP 0 396 650 or DE 298 07 007.3), or polymerized onto moldings (as described in U.S. Pat. No. 5,244,929).

The isobutene is reacted with alcohol to give the corresponding tertiary butyl ether in the reactive distillation, preferably within the temperature range from 10 to 140° C., preferentially from 40 to 90° C., more preferably from 60 to 80° C. (region of the column in which the catalyst is disposed—the bottom temperature of the column may be significantly higher).

In particular, the isobutene is removed by reacting with alcohol (e.g., methanol, ethanol) to give ATBE (MTBE, ETBE). The procedure is in particular as described in DE 101 02 082 for MTBE. The $C_4$ hydrocarbon mixture comprising isobutene is fed into the prereactor together with alcohol. The alcohol is preferably used in excess. In the prereactors, a mixture in which isobutene, alcohol and ATBE are present in equilibrium or virtually in equilibrium is present. This reaction mixture is passed into the reactive distillation column.

In the feed of the reactive distillation column, more alcohol may be present than is needed for the full conversion of the isobutene still present. However, the alcohol excess should be such that a sufficient amount of alcohol is present for the azeotrope of alcohol and $C_4$ hydrocarbons which forms.

Optionally, for example when the alcohol content in the column feed to the reactive distillation column is below the maximum permissible value, additional alcohol may be added. In addition, alcohol may be fed by means of a separate device at the top of the reactive distillation column below or in a liquid distributor.

The reactive distillation column above the catalyst packing preferably has a region of purely distillative separation, more preferably having from 5 to 20, in particular having from 10 to 15 separating stages. The catalyst zone can be estimated at a distillative action of from 1 to 5 theoretical plates per meter of packing height. The separating zone below the catalyst comprises from 12 to 36, in particular from 20 to 30 separating stages. The height of the catalyst zone/reactive zone can be determined as a function of the desired isobutene conversion by simple preliminary experiments. The amount of catalyst is preferably selected at such a level that an isobutene conversion of from 75 to 99%, preferably from 85 to 98% and more preferably from 95 to 97%, based on the isobutene content in the feed to the reactive distillation, is achieved.

The mean temperature in the catalyst zone is, depending on the pressure in the column, preferably from 55° C. to 70° C., more preferably from 58° C. to 67° C. The reactive distillation column is operated at pressures, measured at the top of the column, of from 3 bara to 15 bara, preferably from 5 bara to 11 bara, in particular from 7 bara to 10 bara.

The hydraulic loading in the catalytic packing of the column is preferably from 10% to 110%, preferably from 20% to 70%, of its flood point loading. The term "hydraulic loading" of a distillation column is understood to mean the uniform flow demand on the column cross section by the ascending vapor stream and the refluxing liquid stream. The upper loading limit indicates the maximum loading by vapor and reflux liquid, above which the separating action falls owing to entrainment or accumulation of the reflux liquid by the ascending vapor stream. The lower loading limit indicates the minimum loading, below which the separating action declines or collapses owing to irregular flow or emptying of the column—for example of the trays (Vauck/Müller, "Grundoperationen chemischer Verfahrenstechnik", p. 626, VEB Deutscher Verlag für Grundstoffindustrie.). At the flood point, the shear stresses transferred from the gas to the liquid become so great that the entire amount of liquid is entrained in the form of drops with the gas or that there is phase inversion in the column (J. Mackowiak, "Fluiddynamik von Kolonnen mit modernen Füllkörpern und Packungen für Gas/Flüssigkeitssysteme", Otto Salle Verlag 1991).

The reactive distillation column is preferably operated with reflux ratios of less than 1.5, in particular with those which are greater than 0.4 and less than 1, preferably greater than 0.5 and less than 0.9.

The bottom product of the reactive distillation column preferably consists mainly of ATBE. It preferably contains less than 2500 ppmw of alkyl sec-butyl ether and less than 2500 ppmw of $C_8$ hydrocarbons.

The top product of the reactive distillation can in turn be separated into a $C_4$ hydrocarbon mixture and alcohol, in which case the $C_4$ hydrocarbon mixture preferably contains less than 0.5 ppmw of ATBE and/or TBA.

The alcohol can, for example, be removed by extraction with water. If traces of butadiene have not already been removed before process step a), they can be removed from the raffinate II thus obtained by selective hydrogenation (SHP) (cf. Erdoel & Kohle, Erdgas, Petrochemie (1986), 39(2), 73-8). The $C_4$ hydrocarbon mixture which is obtained from the reactive distillation and has optionally been freed of alcohol can be fed to process step c).

When alcohols other than methanol and ethanol are used for the etherification, the parameters of the reactive distillation change correspondingly.

The ATBE obtained in this embodiment of the process according to the invention can likewise be sent to the end uses described under process step d).

When isobutene is reacted with alcohol in step a) without a reactive distillation having been used, $C_4$ hydrocarbons, if appropriate, together with residual amounts of alcohol, are removed in stage b), preferably by distillation, from the product II in a first step, and, if required, the alcohol is removed extractively from the $C_4$ hydrocarbons III in a second step. When a reactive distillation column is carried out as the last process stage in step a), it is possible to dispense with the distillative separation in step b), and the top product which is obtained in the reactive distillation and is composed of any unconverted alcohol present and unconverted $C_4$ hydrocarbons can either be fed directly to an extraction to remove the alcohol or to step c). The extraction can be performed as described in step e).

Embodiment 3

Oligomerization of Isobutene as the Conversion in Step a)

In a further preferred embodiment of the process according to the invention, the isobutene from the isobutenic technical hydrocarbon mixture is converted in step a) to isobutene oligomers, especially to diisobutene. Isobutene oligomers in the context of the present invention are, in particular, isobutene oligomers such as di-, tri- or tetramers of isobutene. In addition, they may also contain cooligomers with or of 1- or 2-butenes.

The partial iosbetene oligomerization in step a) can be carried out homogeneously, (i.e. using catalysts soluble in the reaction mixture), or heterogeneously, (i.e. using catalysts insoluble in the reaction mixture). The disadvantage of the homogeneous processes is that the catalyst leaves the reactor with the reaction products and unconverted reactants, from which it has to be removed, worked up and disposed of or recycled.

Owing to this high level of separation complexity, the partial oligomerization of the isobutene in step a) is preferably carried out over solid heterogeneous catalysts which are additionally often arranged in a fixed bed so that a complicated catalyst removal is dispensed with.

The solid catalysts used may be acidic substances which are insoluble in the reactant/product mixture. Most of these catalysts belong to one of the following groups:
a) mineral acids (e.g. sulfuric acid or phosphoric acid) on a support material (e.g. alumina or silica),
b) zeolites or other aluminosilicates with or without doping by further metals, especially by transition metals, or
c) acidic ion exchange resins, especially acidic cation exchangers.

Owing to the relatively high selectivity for the formation of isobutene oligomers and the relatively low formation of by-products, preference is given to using acidic ion exchange resins as the catalyst. Suitable ion exchange resins are, for example, those which are prepared by sulfonating phenol/aldehyde condensates or cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. In particular, the cooligomers which are formed by reaction of styrene with divinylbenzene are used as the precursor for the preparation of ion exchange resins with sulfone groups. The properties of these resins, especially specific surface area, porosity, stability, swelling or shrinkage and exchange capacity, can be varied by virtue of the preparation process. The resins may be prepared in gel, macroporous or sponge form. Strongly acidic resins of the styrene/divinylbenzene type are sold, inter alia, under the following trade names: CT 151 from Purolite, Amberlyst 15, Amberlyst 35, Amberlite IR-120, Amberlite 200 from Rohm&Haas, Dowex M-31 from DOW, K 2611, K 2431 from Bayer.

The ion exchange capacity of the resins converted fully to the $H^+$ form is typically between 1 and 2 mol, in particular from 1.5 to 1.9 mol of $H^+$ per liter of moist resin (commercial). In the process of the invention, preference is given to using macroporous resins, for example K 2431 from Bayer, Amberlyst 15 or Amberlyst 3.5 from Rohm & Haas. The pore volume is preferably from 0.3 to 0.6 ml/g, in particular from 0.4 to 0.5 ml/g (based on commercial water-moist resin). The particle size of resin to be used with preference in step a) in the process according to the invention is in the range from 500 µm to 1500 µm, in particular from 600 µm to 1000 µm. The particle size distribution can be selected relatively narrowly or relatively widely. For example, ion exchange resins with very uniform particle size (i.e., monodisperse resins) can be used.

It may be advantageous, in reactors which are flowed through at high linear velocities, to reduce the pressure differential by using monodisperse particles, and, in reactors which are flowed through at a low linear velocity, to achieve the optimal conversion by using particles with a broad particle size distribution. Optionally, the ion exchange resins may be used in the form of moldings, for example cylinders, rings or spheres.

The acidic ion exchange resin is appropriately adjusted to an activity which enables the oligomerization of the isobutene but barely catalyzes the cooligomerization of isobutene with linear butenes, the oligomerization of the linear butanes, or the isomerization of the linear butenes. Moreover, the evolution of heat is thus set to a technically controllable value in the reactor.

The setting of the desired catalyst activity can be done with the aid of moderators. These substances are passed over the catalyst together with the reactant. The moderator used may, for example, be water, alcohols such as tert-butyl alcohol (TBA), methanol, isononanol or ethanol, or ethers such as MTBE or ETBE, in each case as a pure substance or mixtures. The oligomerization in stage a) is therefore preferably carried out in the presence of these moderators. When a moderator are utilized, preference is given to setting molar ratios of from 0.01 to 5 mol, preferably from 0.01 to 1 mol, in particular from 0.01 to 0.7 mol of moderator per mole of isobutene.

In the process according to the invention, it is also possible to use solid sulfonated cation exchangers/exchange resins which have the desired activity without addition of moderators for the oligomerization in step a). These are, in particular, partly neutralized cation exchangers in which some of the acidic hydrogen atoms of the sulfonic acid groups have been exchanged for metal ions, in particular metal ions of the elements of Group 1 to 12 of the Periodic Table. Preference is given to using cation exchangers in which from 1 to 70%, preferably from 5 to 50%, most preferably from 10 to 40% of the acidic hydrogen atoms of the sulfonic acid groups have been exchanged for metal ions. The metal ions which replace the hydrogen atoms may in particular be alkali metal, alkaline earth metal or transition metal ions, for example chromium, manganese, iron, cobalt, nickel, zinc ions and aluminum ions, and also ions of the lanthanide group (rare earths). The acidic hydrogen atoms are preferably replaced by alkali metal ions, in particular sodium ions. It is also possible that the ion exchange resin is laden with two or more different metal ions.

For the preparation of the partly neutralized ion exchange resins, various processes, all of which are described in the technical literature, may be employed. Such processes are described, for example, in EP 1 388 528.

One reactor in the process according to the invention may contain a mixture of ion exchange resins of different reactivity. It is equally possible that one reactor contains catalysts with different activity, for example arranged in layers. When more than one reactor is used, the individual reactors may be filled with catalysts of the same or different activity.

For the industrial performance of the conversion of the isobutenic hydrocarbon mixtures, various variants are possible. The reaction can be carried out batchwise or preferably in continuous reactors, which are typically used in solid/liquid contact reactions. In the case of use of continuous flow reactors, a fixed bed is used usually but not exclusively. Another design as fixed bed reactors is, for example, that of reactors in which the ion exchanger is present suspended in a liquid phase (cf. "Bayer Verfahren" [Bayer process], Erdöl und Kohle, Erdgas, Petrochemie, 1974, 27, No. 5, page 240).

When a fixed bed flow reactor is used, the liquid may flow upward or downward. Usually, preference is given to downward flow of the liquid. A cooling liquid flowing around the reactor may, if appropriate, have the same or opposite flow direction. It is also possible to operate the reactor with product recycling or in straight pass.

In the case of use of tubular reactors, the ratio of length to diameter of the catalyst bed may be varied, either by virtue of the geometric dimensions of the reactor or by virtue of its fill level. With the same amount of catalyst and loading (LHSV), it is thus possible to achieve different superficial velocities.

The reactors used in the industrial process may be operated adiabatically, polytropically or virtually isothermally. Virtually isothermally means that the temperature at any point in the reactor is a maximum of 10° C. higher than the temperature at the reactor inlet. In the case of adiabatic operation of the reactors, it is generally advisable to connect a plurality of reactors in series and preferably to cool between the reactors. Reactors which are suitable for polytropic or virtually isothermal operation are, for example, tube bundle reactors, stirred tanks and loop reactors. It is possible to combine a plurality of reactors, even of different designs. It is additionally possible to operate reactors with recycling of product.

The temperatures at which the oligomerization is conducted may be from 15 to 160° C., preferably from 40 to 110° C.

The reaction can be effected with and without addition of an additional solvent. The solvents used are preferably saturated hydrocarbons, in particular $C_4$, $C_8$ or $C_{12}$ hydrocarbons. Very particular preference is given to the use of isooctane. In the case of addition of solvents, their fraction is from 0 to 60% by mass, preferably from 0 to 30% by mass.

The inventive reaction can be carried out at a pressure equal to or above the vapor pressure of the starting hydrocarbon mixture at the particular reaction temperature, preferably at a pressure below 40 bar, i.e. the isobutenic hydrocarbon mixtures are present fully or partly in liquid phase during the oligomerization. When the reaction is to be carried out fully in the liquid phase, the pressure should preferably be from 2 to 4 bar higher than the vapor pressure of the reaction mixture in order to prevent evaporation problems in the reactors.

Even when the reaction is conducted at a pressure at which the reaction mixture is not present fully in liquid form (for example in a reactive distillation or in process variants analogous to U.S. Pat. No. 5,003,124), the oligomerization by the process according to the invention nevertheless takes place in the liquid phase, i.e. over "moist", i.e. liquid-wetted, catalyst.

The overall conversion of isobutene to oligomers may be adjusted via the type and amount of the catalyst used, the reaction conditions established, and number of reactors. In the process according to the invention, preferably from 30 to 95%, preferentially from 50 to 80%, more preferably from 55 to 70%, of the isobutene present in the reactant is oligomerized.

The reaction mixture of the partial isobutene oligomerization can be worked up in different ways. The products II (oligomers) and, where present hydrocarbons having from 5 to 7 carbon atoms, are removed from unconverted $C_4$ hydrocarbons III in step b) by distillation. The distillation is preferably conducted at a pressure of from 1 to 10 bara, more preferably at a pressure of from 4 to 7 bara. The temperatures in the bottom are preferably from 120 to 220° C., more preferably from 170 to 200° C. The reflux ratio is preferably set to values of from 0.1 to 1.5, preferably from 0.3 to 1.0. The distillation is preferably carried out in a column having a number of trays of from 20 to 40, preferably from 25 to 35. The unconverted $C_4$ hydrocarbons thus removed are treated further in the inventive step c).

The oligomer fraction removed contains mainly $C_8$ hydrocarbons and may, where appropriate, comprise the moderators used. In addition to the diisobutene, they may also contain codimers and higher oligomers ($C_{12}$, $C_{16+}$). The fraction of cooligomers is preferably below 50% by mass, more preferably below 25% by mass. This fraction may be separated in further distillation steps. For example, it is possible to remove a fraction comprising highly pure diisobutene in order to use it separately, for example for chemical syntheses. For use as a fuel component for gasoline engines, it may be necessary to remove high-boiling components (preferably boiling point >220° C.).

It is also possible to fully or partly hydrogenate the butene oligomers, especially the $C_8$ olefins. Methods for hydrogenating the products of the oligomerization to the corresponding paraffins are sufficiently well known to those skilled in the art. Common methods for hydrogenating olefins are described, for example, in F. Asinger, "Chemie und Technologie der Monoolefine"[Chemistry and technology of the monoolefins], Akademie Verlag, Berlin, 1957, page 626-628 or DE 197 19 833.

In a preferred embodiment, the hydrogenation is carried out in the liquid phase over a solid catalyst insoluble in the hydrogenation mixture. The hydrogenation catalysts used are preferably supportive catalysts which consist of an inorganic support and contain platinum and/or palladium and/or nickel as the active metal. The temperature at which the hydrogenation is carried out is preferably in the range from 10 to 250° C. and the pressure between 1 and 100 bar.

After the hydrogenation, further fractions can be obtained by distillative separation. Fuel additives are obtainable from these and from the unhydrogenated fractions by blending. Some fractions can also be used as solvents.

Embodiment 4

Reaction of Isobutene in Step a) with Formaldehyde

In a further preferred embodiment of the process according to the invention, the isobutene is reacted in step a) with formaldehyde or a formaldehyde derivative. Depending on the reaction conditions, the main product obtained is 4,4-dimethyl-1,3-dioxane or 3-methyl-3-buten-1-ol. The process has been known for some time in the literature. Information on this process can be found, for example, in the current edition of Ullmann's Encyclopedia of Industrial Chemistry, Wiley-VCH Verlag, under "isoprene", and the references cited there, in Weissermel, Arpe, Industrielle Organische Chemie [Industrial organic chemistry], VCH, 4th edition, 1994, pages 127 to 131, and in W. Swodenk, W. Schwerdtel, P. Losacker, Erdöl und Kohle-Erdgas-Petrochemie, 1970, 23, 641 to 644. The two products, 3-methyl-3-buten-1-ol and 4,4-dimethyl-1,3-dioxane (1,3-dioxane) are used mainly for the preparation of isoprene. The 1,3-dioxane obtainable by reacting isobutene with formaldehyde can be converted to isoprene, for example, by cleavage in the gas phase at from 200 to 300° C. over an acidic catalyst, for example phosphoric acid on a support, in which case half of the amount of formaldehyde required to prepare the 1,3-dioxane can be recovered again (cf. DE 196 31 005).

The 3-methyl-3-buten-1-ol, which can also be obtained from the 1,3-dioxane by elimination of formaldehyde, can, for example, also be used to prepare 3-methylbutan-1-ol, from which 3-methyl-1-butene can be obtained in turn by water elimination.

The isobutene can be reacted either directly with the formaldehyde, or as a solution of formaldehyde in water or another solvent, or with a suitable formaldehyde derivative. Suitable formaldehyde derivatives are, for example, methylal or dioxolane. The reaction can be effected with or without use of catalysts and is possible both in the liquid phase and in the gas phase (cf. DE 15 93 851; DE 17 68 057; DE 12 75 049; U.S.

Pat. No. 2,308,192; FR 155 6915; Studies in Surface Science and Catalysis, Vol. 125, 199, 507 to 514). The reaction is preferably carried out in the liquid phase using catalysts. The catalysts used are preferably metal catalysts, Brønsted and Lewis acids. Particular preference is given to using transition metal catalysts and acidic ion exchange resins, as are also used in embodiment 1 of process step a).

The isobutene conversion achieved in the reaction with formaldehyde is preferably from 30 to 90%, more preferably from 40 to 70%.

The reaction mixture of the reaction in embodiment 4 of step a) is worked up differently depending on the type of reaction selected. When a plurality of phases are present after the reaction, for example an aqueous phase and an organic phase which contains mainly the unconverted $C_4$ hydrocarbons and the main products of the reaction, a phase separation is carried out first. To remove residual amounts of formaldehyde, a water scrubbing can subsequently be effected. The products II (allyl alcohols, 1,3-dioxanes or 1,3-diols) and, if appropriate, hydrocarbons having from 5 to 7 carbon atoms are then removed from unconverted $C_4$ hydrocarbons III in step b) appropriately by distillation. At least in one distillation column, the unconverted $C_4$ hydrocarbons are obtained as the top product. This distillation is effected preferably at a pressure of from 1 to 11 bara, more preferably from 3 to 8 bara and most preferably from 4 to 7 bara. The temperature in the top of the column is preferably from 40 to 60° C., preferentially from 45 to 50° C. In the distillation, a reflux ratio of from 0.5 to 2, preferably of approx. 1 is preferably established. When, in addition to the unconverted $C_4$ hydrocarbons, a second aqueous phase is obtained at the top of the column, the second aqueous phase is preferably removed in a top decanter. The distillation is preferably carried out in a column which has at least a number of 20 theoretical plates, preferably from 25 to 50 and more preferably from 30 to 40 theoretical plates. The unconverted hydrocarbons III thus removed are treated further in the inventive step c).

The fractions obtained in the distillation, which may comprise 3-methyl-3-buten-1-ol and/or 4,4-dimethyl-1,3-dioxane, may be directly converted to isoprene as described above or converted to isoprene after further purification, for example a further distillation or extraction.

Feedstocks

In the inventive process, all technical $C_4$ hydrocarbon mixtures typically available may be used. Suitable isobutenic $C_4$ streams are, for example, light petroleum fractions from crackers (for example steamcrackers, hydrocrackers, catcrackers), mixtures from Fischer-Tropsch syntheses, mixtures from the dehydrogenation of butanes, mixtures from skeletal isomerization of linear butenes and mixtures formed by metathesis of olefins. These techniques are described in the technical literature (K. Weissermel, H. J. Arpe, Industrielle Organische Chemie, Wiley-VCH, 5th edition, 1998, pages 23-24; 65-99; 122-124).

Preference is given to using $C_4$ fractions from steamcrackers which are operated primarily for the production of ethene and propene and in which the raw materials used are, for example, refinery gases, naphtha, gas oil, LPG (liquefied petroleum gas) and NGL (natural gas liquid), or $C_4$ fractions from catcrackers. The $C_4$ cuts obtained as a by-product contain, depending on the cracking process, different amounts of isobutene. Further main constituents are 1,3-butadiene, 1-butene, c-2-butene, t-2-butene, n-butane and i-butane. Typical isobutene contents in the $C_4$ fraction are from 18 to 35% by mass in the case of $C_4$ fractions from steamcrackers, and from 10 to 20% by mass in the case of fluid catcrackers (FCC).

For the inventive process, it is advantageous to remove polyunsaturated hydrocarbons such as 1,3-butadiene from the use mixture. This can be done by known processes, such as by extraction, extractive distillation or complex formation (cf. K. Weissermel, H. J. Arpe, Industrielle Organische Chemie, Wiley-VCH, 5th edition, 1998, pages 119 to 121).

One alternative to the removal of the polyunsaturated hydrocarbons is a selective chemical conversion. For example, 1,3-butadiene can be hydrogenated selectively to linear butenes, as described, for example, in EP 0 523 482. It is also possible to remove the 1,3-butadiene at least partly by selective conversions of the 1,3-butadiene, for example dimerization to cyclooctadiene, trimerization to cyclododecadiene, polymerization or telomerization reactions. When a crack-$C_4$ cut was used as the raw material, a hydrocarbon mixture (raffinate I or hydrogenated crack-$C_4$ ($HCC_4$)) always remains and contains mainly the saturated hydrocarbons, n-butane and is obutane and the olefins isobutene, 1-butene and 2-butenes.

In the inventive process, in an additional purification stage which is connected upstream of one or more of process steps a), b), c), d), e) or f), polyunsaturated hydrocarbons present in the $C_4$ hydrocarbon streams are preferably catalytically and selectively hydrogenated. More preferably, such a purification stage is provided at least before process step a) and/or c), especially when it cannot be ruled out that the technical $C_4$ hydrocarbon streams used comprise polyunsaturated hydrocarbons.

The polyunsaturated hydrocarbons are mainly 1,3-butadiene; 1,2-butadiene, butenyne and 1-butyne are present, if at all, in a significantly smaller amount. The hydrogenation can be effected in a one-stage or multistage hydrogenation process in the liquid phase over a palladium catalyst. To lower the content of 1,3-butadiene below preferably 1000 ppmw, a moderator which increases the selectivity of the palladium catalyst is added in the last stage of the hydrogenation. The moderator used is preferably carbon monoxide which is added in a fraction of from 0.05 to 100 ppm by mass (ppmw). The content of polyunsaturated hydrocarbons in the feed to this stage should be below 1%, preferably below 0.5%. In the literature, this type of selective hydrogenation of residual contents of 1,3-butadiene is known under the name SHP (selective hydrogenation process) (cf. EP 0 081 041; Erdöl, Kohle, Erdgas, Petrochem. 1986, 39, 73).

When amounts of more than 1% of polyunsaturated hydrocarbons such as 1,3-butadiene are present in the isobutenic $C_4$ streams, they are preferably converted in upstream hydrogenations. These hydrogenations are preferably carried out in the liquid phase over a palladium catalyst. Depending on the content of unsaturated hydrocarbons, the hydrogenation may be carried out in a plurality of stages. For the conversion of crack-$C_4$ from a steamcracker with a content of 1,3-butadiene of typically from 38 to 45%, a two-stage version of the hydrogenation has been found to be useful. In this case, individual or all stages may be equipped with partial product recycling. In the effluent, concentrations of 1,3-butadiene of less than 1% are thus obtainable, so that a further conversion can be effected in a selective hydrogenation (SHP).

The hydrocarbon mixtures with isobutene and linear butenes used in the inventive process preferably have the following compositions, a hydrogenation or selective hydrogenation being carried out before one of steps a) to d), preferably before step c), depending on the content of unsaturated hydrocarbons.

TABLE 1

Typical compositions of technical hydrocarbon mixtures which can be used in the inventive process.

|  | Steamcracker | | Steamcracker | | Catcracker | |
| --- | --- | --- | --- | --- | --- | --- |
| Component | $HCC_4$ | $HCC_4$/SHP | Raff. I | Raff. I/SHP | $CC_4$ | $CC_4$/SHP |
| Isobutane [% by mass] | 1-4.5 | 1-4.5 | 1.5-8 | 1.5-8 | 37 | 37 |
| n-Butane [% by mass] | 5-8 | 5-8 | 6-15 | 6-15 | 13 | 13 |
| trans-Butene [% by mass] | 18-21 | 18-21 | 7-10 | 7-10 | 12 | 12 |
| 1-Butene [% by mass] | 35-45 | 35-45 | 15-35 | 15-35 | 12 | 12 |
| Isobutene [% by mass] | 22-28 | 22-28 | 33-50 | 33-50 | 15 | 15 |
| cis-Butene [% by mass] | 5-9 | 5-9 | 4-8 | 4-8 | 11 | 11 |
| 1,3-Butadiene [ppmw] | 500-8000 | 0-50 | 50-8000 | 0-50 | <10 000 | 0-50 |

Explanation $HCC_4$: typical of a $C_4$ mixture which is obtained from the crack-$C_4$ of a steamcracker (high severity) after the hydrogenation of the 1,3-butadiene without additional moderation of the catalyst.
$HCC_4$/SHP: $HCC_4$ composition in which residues of 1,3-butadiene have been reduced further in an SHP.
Raff. I (raffinate I): typical of a $C_4$ mixture which is obtained from the crack-$C_4$ of a steamcracker (high severity) after the removal of the 1,3-butadiene, for example by an NMP extractive rectification.
Raff. I/SHP: Raff. I composition in which residues of 1,3-butadiene have been reduced further in an SHP.
$CC_4$: typical composition of a crack-$C_4$ which is obtained from a catcracker.
$CC_4$/SHP: $CC_4$ composition in which residues of 1,3-butadiene have been reduced further in an SHP.

Among others, the raffinate I or $HCC_4$ is an isobutenic hydrocarbon mixture used with preference within the context of this invention. Since plants for working up $C_4$ hydrocarbons are generally constructed as a strand (integrated system of a plurality of plants), it is, however, possible that the raffinate I or $HCC_4$ passes through one or more other process stage(s) before entry into the inventive process. This process stage or these process stages may, for example, also be a process or process step(s) as have been described in the embodiments for process step a). $C_4$ hydrocarbon mixtures usable in the inventive process may also be those as obtained from processes as per the embodiments of process step a) and subsequent separation as per process step b). In particular, those mixtures as obtained in the preparation of TBA from isobutene after removal of the TBA may also be used. In this way, an individually adapted overall concept for workup with the appropriate product portfolio can be realized in each case.

Typical processes which can be connected upstream of the inventive processes are water scrubbings, purification processes in adsorbers, drying processes and distillations.

Water Scrubbing

A water scrubbing can fully or partly remove hydrophilic components, for example nitrogen components, from the technical hydrocarbon mixture containing isobutene and linear butenes. Examples of nitrogen components are acetonitrile or N-methylpyrrolidone (which can stem, for example, from a 1,3-butadiene extractive distillation). Oxygen compounds (for example acetone from FCC) may also be removed partly by means of a water scrubbing. After a water scrubbing, the isobutenic hydrocarbon stream is saturated with water. In order to avoid biphasicity in the downstream process steps in the reactor, the reaction temperature there should be approx. 10° C. above the temperature of the water scrubbing.

Adsorbents

Adsorbents are used to remove impurities. This may be advantageous, for example, when noble metal catalysts are used in one of the process steps. Often, nitrogen or sulfur compounds are removed by means of upstream adsorbers. Examples of adsorbents are aluminas, molecular sieves, zeolites, activated carbon, aluminas impregnated with metals. Adsorbents are sold by various companies, for example Alcoa (Selexsorb®).

Drying

Any water present in the isobutenic hydrocarbon mixture, which may stem, for example, from the water scrubbing, can be removed by known processes for drying. Suitable processes are, for example, the distillative removal of the water as an azeotrope. Often, an azeotrope containing $C_4$ hydrocarbons may be utilized or azeotroping agents may be added.

The drying of the hydrocarbon mixture may be advantageous for various reasons, for example to reduce the formation of alcohols (mainly tert-butyl alcohol) in step a) in the case of embodiments 2 and 3, to prevent (uncontrolled) water moderation in the butene oligomerization (embodiment 3 of step a)), to avoid technical problems as a result of separation of water or to prevent ice formation at low temperatures (for example in the course of intermediate storage).

Distillation

Distillation steps may be utilized to remove impurities (for example low boilers such as $C_3$ hydrocarbons, and high boilers such as $C_5$ hydrocarbons) or to obtain fractions with different isobutene concentrations. This can be done either directly with the raffinate I or the $HCC_4$ or after one or more other process stage(s) have been passed through. Direct distillation of the raffinate I or of the $HCC_4$ makes it possible, for example, to separate into a relatively isobutene-rich fraction depleted in 2-butenes and n-butane.

Depending on the composition of the technical hydrocarbon mixture to be used and/or on the purities of the target products, the technical hydrocarbon mixture may thus be used directly in step a) of the inventive process or else only after a pretreatment by one or more of the aforementioned processes.

Examples

The present invention is described by way of example in the examples herein after. Obviously, numerous modifications and variations of the present invention are possible in light of the above listed teachings. It is therefore to be understood that, within the scope of the appended claims, the invention may be practiced otherwise than as specifically described herein.

The example calculations which follow were carried out with the simulation program ASPEN Plus. In order to obtain transparent, reproducible data, only generally available substance data were used. The use of kinetic approaches was deliberately dispensed with. In all variants, the use of a reactive distillation was also dispensed with. These simplifications make it readily possible for the person skilled in the art to comprehend the calculations. Although the methods used do not have sufficient precision for the design of industrial plants, the qualitative differences in the arrangements are detected correctly. In all variants shown, the isobutene conversion was increased by use of one or more reactive distillation(s).

The reactors and MTBE columns were calculated with the "UNIFAC-DMD" property method. For the calculation of the $C_4$ columns, an equation of state was used with the "Peng-Robinson" property method. The following assumptions were made:

All reactors attained the equilibrium calculated with UNIFAC fully at 50° C.

The columns were calculated with a reflux ratio of 0.8.

In the MTBE columns, a $C_4$/methanol azeotrope was removed via the top. The MeOH was scrubbed out with water in extractors, which were modeled as simple one-component splitters.

The MeOH-water mixture obtained from the extractors was worked up by distillation in a further column K-MeOH which was not shown in the connection diagrams. Both products of the K-MeOH were recirculated into the process.

The examples calculated were based on a mix of typical $C_4$ raw materials obtainable on the market. The raw material stream of 10 t/h contained 28% by mass of isobutene and 35% by mass of 1-butene. The isobutene was to be removed chemically from this stream by MTBE synthesis, and a 1-butene amount of 3 t/h with a purity greater than 99.6% was to be prepared. This corresponded to a 1-butene yield of approx. 85%. In the 1-butene product, a maximum of 2000 ppm of isobutene were to be present. Table 2 compares the composition of the $C_4$ raw material stream of the desired 1-butene specification. The amount of methanol used in the examples was 1900 kg/h (approx. 19% excess).

TABLE 2

Composition of the $C_4$ raw material stream and desired specification of the 1-butene (percentage data are percentages by mass)

| Component | $C_4$ feed | | 1-Butene | |
|---|---|---|---|---|
| | [kg/h] | [%] | [kg/h] | [%] |
| Isobutane | 500 | 5.0 | 3 | 0.1 |
| 1-Butene | 3500 | 35.0 | 2990 | 99.7 |
| cis-2-Butene | 1400 | 14.0 | | 0.0 |
| trans-2-Butene | 800 | 8.0 | | 0.0 |
| Isobutene | 2800 | 28.0 | 6 | 0.2 |
| n-Butane | 1000 | 10.0 | 1 | 0.0 |
| Total | 10000 | 100 | 3000 | 100 |

Three process variants of different suitability for achieving the objective were calculated below.

The simplest variant A was a one-stage process which is intended to serve as a comparative standard. According to FIG. 7, methanol and isobutene were reacted to equilibrium in a reaction stage R-a. In the distillation stage K-b1, the MTBE (II) was obtained as a bottom product. The column had 50 theoretical plates and was operated at a reflux ratio of 0.8. The distillate of this column was a $C_4$/MeOH azeotrope from which the MeOH could be scrubbed out, for example, with water in an extraction column K-b2. The raffinate of the extraction column K-b2 was fed to a $C_4$ column analogous to K-c1 in FIG. 5, in which isobutane, isobutene and 1-butene were removed via the top. The distillate IV of K-c1 was passed directly into a further column K-f1 according to FIG. 6 in which principally isobutane was removed via the top. The bottom product obtained was a 1-butene-rich fraction which contained the majority of the isobutene unconverted in R-a.

The 1-butene prepared with variant A contained 1.9% by mass of isobutene, see Table 3, and thus did not achieve the target of 2000 ppm. Further measures are needed to increase the conversion.

Another process improvement was examined as variant B and is shown in FIG. 8. In order to drive the equilibrium further in the MTBE direction, a further reactor R-b2 which reacted the residual isobutene with the MeOH removed in K-b1 as an azeotrope D-b1 via the top was connected downstream of the column K-b1. The MTBE formed was removed in a further $C_4$/MTBE distillation K-b3. This required the entire $C_4$ stream to be distilled via the top for a second time. The energy demand of K-b3 was thus virtually just as great as that of K-b1. Subsequently, the extraction K-b2 and the 1-butene distillation K-c1 and K-f1 were performed as in variant A. The 1-butene product with less than 500 ppm then achieved the required product specification. However, the total energy demand of the plant is about 12% higher compared to variant A (see Table 4).

In the process according to the invention, variant C according to FIG. 9, a second reaction, distillation and extraction stage R-d, K-e1 and K-e2 was connected between the two $C_4$ columns K-c1 and K-f1. This had the advantage that the greater part of the feed III of K-c1 is obtained as the bottom product V and only the part of the $C_4$ stream which was to be worked up in K-f1 to give pure 1-butene had to be distilled for a second time. In the present case, the energy demand of K-b2 in variant B was more than twice as high as the energy demand of K-e1 in variant C. A disadvantage of variant C was that a second extraction column K-e2 had to be built. Since the throughput through R-d1, K-e1 and K-e2, though, was less than half of the throughput through K-b3 in variant B, the total capital costs were correspondingly lower. The amount of isobutene in the 1-butene product in the calculated example was likewise less than 500 ppm.

Table 3 shows the conversions achieved in the three variants. While variant A clearly fails to meet the quality of the 1-butene product, an on-spec product was calculated in the two two-stage processes B and C. The increased isobutene conversion was achieved in both variants by distillative removal of the MTBE reaction product before a second reaction stage and hence by increased energy input. However, the inventive arrangement of the second reaction stage in variant C between the two $C_4$ columns K-c1 and K-f1 reduced the amount of the stream to be distilled additionally to less than half. This leads to significant savings in energy demand and investment.

TABLE 3

Conversions and 1-butene qualities of the three variants

|  | Variant A, one-stage | Variant B, two-stage | Variant C, two-stage |
|---|---|---|---|
| Isobutene in the feed [kg/h] | 2800 | 2800 | 2800 |
| Isobutene after stage 1 [kg/h] | 65.6 | 65.6 | 65.6 |
| Stage 1 conversion [%] | 97.7 | 97.7 | 97.7 |
| Isobutene after stage 2 [kg/h] | 0.0 | 0.9 | 0.9 |
| Stage 2 conversion [%] | 0.0 | 98.6 | 98.6 |
| Overall conversion [%] | 97.7 | 99.97 | 99.97 |
| Isobutene in the 1-butene [ppm] | 19 130 | <500 | <500 |
| 1-Butene purity [%] | 97.8 | 99.7 | 99.7 |

Table 4 compares the numerical energy demands of all three variants. In all three arrangements, the energy demand of columns K-b1, K-c1 and K-f1 is virtually identical. Although variant A had the lowest total energy demand, the product specification was not met. In variant B, double the amount of $C_4$ had to be distilled via the top in the MTBE part, and its energy demand was therefore 12% higher than in variant A. In contrast, variant C showed a way of achieving the required conversion with energy demand increased by only about 6%.

TABLE 4

Energy demand of the three variants

|  | Variant A, one-stage | Variant B, two-stage | Variant C, two-stage |
|---|---|---|---|
| Q for K-b1 [kW] | 1353 | 1353 | 1353 |
| Q for K-b3 [kW] | 254 | 233 | 328 |
| Q for K-c1 [kW] | 3530 | 3493 | 3530 |
| Q for K-b2 [kW] |  | 1333 | 620 |
| Q for K-e1 [kW] |  |  |  |
| Q for K-f1 [kW] | 3741 | 3672 | 3669 |
| Q for MTBE [kW] | 1608 | 2919 | 2300 |
| Total Q [kW] | 8878 | 10 084 | 9498 |
| Additional ΔQ demand for MTBE [%] | 0 | 81.6 | 43.1 |
| Total additional ΔQ demand [%] | 0 | 12.0 | 6.5 |

The designations in figures FIG. 1 to FIG. 9 have the following meanings:
(a) Partial isobutene conversion to products II
(b) $C_4$ hydrocarbons III removal
(c) Distillative separation of III into IV and V
(d) Etherification of isobutene with alcohol VI
(e) Removal of t-butyl ether VII
(f) 1-Butene removal
I Technical mixture of $C_4$ hydrocarbons
II Products from the isobutene conversion
III Remaining $C_4$ hydrocarbons
IV 1-Butenic and isobutenic fraction
V Isobutene-free fraction comprising 2-butenes and n-butanes
VI Alcohol
VII Alkyl tert-butyl ether
VIII $C_4$ hydrocarbons from stage e)
D-b1 Distillate of K-b1
D-b3 Distillate of K-b3
D-c1 Aqueous phase obtained in the condensation at the top of K-c1
D-e1 Top product of K-e1
D-f1 Distillate of K-f1, organic phase
D-f2 Low boilers
E-b1 Extractant inlet
E-b2 Extractant outlet
E-e1 Extractant inlet
E-e2 Extractant outlet
K-b1 Distillation
K-b2 Extraction column
K-b3 Distillation
K-c1 Column for separating the $C_4$ hydrocarbons
K-e1 Column for removing the ether
K-e2 Extraction column
K-f1 Column for 1-butene removal
K-f2 Isobutane removal column
R-a Reactor
R-a1 Reactor
R-a2 Reactor
R-a3 Reactor
R-b2 Etherification reactor (comparative example)
R-d1 Etherification reactor
S-f1 1-Butene
S-f2 Isobutane
W-b1 Bottom evaporator
W-b2 Condenser
W-b3 Bottom evaporator
W-b4 Condenser
W-c1 Bottom evaporator
W-c2 Condenser
W-e1 Bottom evaporator
W-e2 Condenser
W-f1 Bottom evaporator
W-f2 Condenser
W-f3 Bottom evaporator
W-f4 Condenser The above written description of the invention provides a manner of making and process of using it such that any person skilled in this art is enabled to make and use the same, this enablement being provided in particular for the subject matter of the appended claims, which make up part of the original description.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges withing a numerical limit or range are specifically included as explicitly written out. Terms such as "contain(s)" and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed therein.

The invention claimed is:
1. A process for preparing 1-butene from a technical mixture of $C_4$ hydrocarbons I, wherein the technical mixture of $C_4$ hydrocarbons comprise at least 1-butene, isobutene, n-butane and cis and trans 2-butenes, comprising a) reacting a portion of the isobutene present in the technical mixture to give at least one product II which boils at higher than 30° C. at standard pressure, and unconverted $C_4$ hydrocarbons III, b) removing the unconverted $C_4$ hydrocarbons III from a) by a thermal separation process, c) distillatively separating the $C_4$ hydrocarbons III into a fraction IV comprising the 1-butene and the isobutene, and a virtually isobutene-free fraction V comprising the cis and trans 2-butenes and the n-butane, d) reacting the isobutene present in fraction IV with at least one alcohol VI in the presence of at least one acidic catalyst to give at least one tert-butyl ether VII, and unconverted $C_4$ hydrocarbons VIII, e) removing the unconverted $C_4$ hydrocarbons VIII from d) and f) distillatively removing the 1-butene from the $C_4$ hydrocarbons VIII obtained in e).

2. The process of claim 1,
wherein
the acid-catalyzed etherification in d) is carried out in at least one reaction stage, and wherein one reaction stage of the at least one reaction stage comprises a reactive distillation.

3. The process according of claim 1,
wherein
the acid-catalyzed etherification in d) is carried out in at least two reaction stages, and wherein at least the last reaction stage of the at least two reaction stages comprises a reactive distillation.

4. The process of claim 1,
wherein
the at least one alcohol in d) is methanol or ethanol.

5. The process of claim 4,
wherein
the at least one alcohol in d) is methanol.

6. The process of claim 4,
wherein
the at least one alcohol in d) is ethanol.

7. The process of claim 1,
wherein
the unconverted C4 hydrocarbons VII in e) comprise a residual amount of alcohol, and
wherein
the residual amount of alcohol is scrubbed out, in e), in an extraction step with water.

8. The process of claim 1, further comprising an additional purification,
wherein
the polyunsaturated hydrocarbons present in the $C_4$ hydrocarbon stream are hydrogenated catalytically, and
wherein the additional purification is preceded by at least one of a), b), c) or d).

9. The process of claim 8,
wherein
the catalytic hydrogenation of the polyunsaturated hydrocarbons comprises at least two reaction stages, and
wherein
at least the last reaction stage is carried out in the presence of from 0.05 to 100 ppmw of CO.

10. The process of claim 1,
wherein
the reaction of a portion of the isobutene, in a), results in a conversion of the portion of the isobutene of over 70%.

11. The process of claim 1,
wherein
the reaction of the portion of the isobutene in a) is carried out with water or an alcohol as a co-reactant and
wherein
the reaction of a portion of the isobutene results in a conversion of the portion of isobutene of over 75%.

12. The process of claim 1,
wherein
the portion of isobutene reacted in a) is reacted under acidic catalysis with at least one alcohol to give at least one alkyl tert-butyl ether (ATBE) or
wherein
the portion of isobutene reacted in a) is reacted with water under acidic catalysis to give a tertiary butyl alcohol (TBA).

13. The process of claim 12,
wherein
the acidic catalyst comprises at least one ion exchange resin.

14. The process of claim 12,
wherein
the portion of isobutene reacted in a) is reacted with water under acidic catalysis to give a tertiary butyl alcohol (TBA).

15. The process of claim 12,
wherein
the portion of isobutene reacted in a) is reacted under acidic catalysis with at least one alcohol to give at least one alkyl tert-butyl ether (ATBE).

16. The process of claim 15,
wherein the at least one alcohol is methanol.

17. The process of claim 15,
wherein the at least one alcohol is ethanol.

18. The process of claim 15,
wherein,
after the portion of the isobutene has been reacted with the at least one alcohol in a), the thermal separation process in b) comprises
removal, by distillation, of the unconverted $C_4$ hydrocarbons together with a residual amount of the at least one alcohol, and
removal of the residual amount of the at least one alcohol, by extraction, from the unconverted $C_4$ hydrocarbons.

19. The process of claim 18,
wherein
the same at least one alcohol is used in stage a) and in stage d).

20. The process of claim 19,
wherein
the tert-butyl ether VII obtained in e), in the course of removal of the $C_4$ hydrocarbons VIII, is returned together with excess alcohol fully or partly into a), b), or a) and b).

21. The process of claim 14,
wherein
after the portion of the isobutene has been reacted with water in a), the thermal separation process, in b) is a distillation
wherein
the unconverted $C_4$ hydrocarbons are removed from the products II.

22. The process of claim 21,
wherein
after the portion of the isobutene has been reacted with water in a), the unconverted $C_4$ hydrocarbons, in b), are removed together with a little water.

23. The process of claim 1, wherein
the reacting of a portion of the isobutene in a) comprises converting the portion of the isobutene to diisobutene.

24. The process of claim 23, wherein
the reacting in a) is effected under acidic catalysis.

25. The process of claim 23, wherein
the reacting in a) is effected in the presence of a cation exchanger.

26. The process of claim 25, wherein
the cation exchanger comprises acidic hydrogen atoms, and
wherein
a portion of the acidic hydrogen atoms have been exchanged for metal ions of at least one metal of Groups 1 to 12 of the Periodic Table.

27. The process of claim 26, wherein
from 1 to 70% of the acidic hydrogen atoms of the ion exchanger have been exchanged for metal ions of at least one metal of Groups 1 to 12 of the Periodic Table.

28. The process of claim 27, wherein
the thermal separation in b) comprises distillation of the unconverted $C_4$ hydrocarbons III from the products II.

29. The process of claim 1, wherein
the portion of the isobutene is reacted in a) with formaldehyde to give 4,4-dimethyl-1,3-dioxane or 3-methyl-3-buten-1-ol.

30. The process of claim 29, wherein
the portion of the isobutene is reacted in a) with formaldehyde to give 4,4-dimethyl-1,3-dioxane.

31. The process of claim 29, wherein
the portion of the isobutene is reacted in a) with formaldehyde to give 3-methyl-3-buten-1-ol.

32. The process of claim 1, wherein
the 1-butene obtained by distillation in f) has an isobutene content of less than 5000 ppmw.

* * * * *